United States Patent
Konopacki et al.

(10) Patent No.: US 11,737,471 B2
(45) Date of Patent: *Aug. 29, 2023

(54) PRODUCTS HAVING HIGH EFFICACY OMEGA-6/OMEGA-3 BALANCED POLYUNSATURATED FATTY ACIDS

(71) Applicant: OMEGA FOODS, LLC, Two Rivers, WI (US)

(72) Inventors: Andrew Konopacki, Denmark, WI (US); Michael Gurin, Glenview, IL (US)

(73) Assignee: OMEGA FOODS, LLC, Two Rivers, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/156,907

(22) Filed: Jan. 19, 2023

(65) Prior Publication Data

US 2023/0148619 A1 May 18, 2023

Related U.S. Application Data

(63) Continuation of application No. 17/860,066, filed on Jul. 7, 2022, now Pat. No. 11,589,594, which is a continuation of application No. 17/497,843, filed on Oct. 8, 2021, now Pat. No. 11,490,630, which is a continuation of application No. 17/175,457, filed on Feb. 12, 2021, which is a continuation-in-part of
(Continued)

(51) Int. Cl.

| | | |
|---|---|---|
| A23L 27/60 | (2016.01) |
| A23L 33/115 | (2016.01) |
| A23C 9/123 | (2006.01) |
| A21D 2/16 | (2006.01) |
| A23G 9/32 | (2006.01) |
| A23D 7/00 | (2006.01) |
| A23C 19/09 | (2006.01) |
| A23C 19/076 | (2006.01) |
| A23D 7/005 | (2006.01) |
| A61K 31/201 | (2006.01) |
| A23L 11/00 | (2021.01) |
| A61K 45/06 | (2006.01) |
| A61K 31/202 | (2006.01) |
| A23D 7/01 | (2006.01) |
| A23L 25/10 | (2016.01) |
| A23L 23/00 | (2016.01) |
| A23L 13/50 | (2016.01) |
| A23L 9/10 | (2016.01) |
| A23L 21/10 | (2016.01) |
| A61K 31/355 | (2006.01) |
| A23L 19/18 | (2016.01) |
| A23L 33/12 | (2016.01) |
| A23L 2/68 | (2006.01) |
| A23L 15/00 | (2016.01) |
| A23L 7/109 | (2016.01) |
| A23L 7/117 | (2016.01) |
| A23L 19/00 | (2016.01) |
| A23L 2/02 | (2006.01) |

(52) U.S. Cl.
CPC ............... *A23C 9/123* (2013.01); *A21D 2/16* (2013.01); *A21D 2/165* (2013.01); *A23C 19/076* (2013.01); *A23C 19/0904* (2013.01); *A23D 7/001* (2013.01); *A23D 7/003* (2013.01); *A23D 7/0053* (2013.01); *A23D 7/011* (2013.01); *A23G 9/327* (2013.01); *A23L 2/02* (2013.01); *A23L 2/68* (2013.01); *A23L 7/109* (2016.08); *A23L 7/117* (2016.08); *A23L 9/10* (2016.08); *A23L 11/05* (2016.08); *A23L 13/50* (2016.08); *A23L 15/20* (2016.08); *A23L 19/09* (2016.08); *A23L 19/18* (2016.08); *A23L 21/10* (2016.08); *A23L 23/00* (2016.08); *A23L 25/10* (2016.08); *A23L 27/60* (2016.08); *A23L 27/63* (2016.08); *A23L 33/115* (2016.08); *A23L 33/12* (2016.08); *A61K 31/201* (2013.01); *A61K 31/202* (2013.01); *A61K 31/355* (2013.01); *A61K 45/06* (2013.01); *A23V 2002/00* (2013.01)

(58) Field of Classification Search
None
See application file for complete search history.

(56) References Cited

U.S. PATENT DOCUMENTS

| | | |
|---|---|---|
| 4,357,343 A | 11/1982 | Madsen et al. |
| 5,064,677 A | 11/1991 | Cain |

(Continued)

FOREIGN PATENT DOCUMENTS

| | | |
|---|---|---|
| FR | 2909839 A1 | 6/2008 |
| JP | 02049593 A | 2/1990 |

(Continued)

OTHER PUBLICATIONS

Sacks et al., Controlled Trial of Fish Oil for Regression of Human Coronary Atherosclerosis, JACC vol. 25, No. 7, Jun. 1995: 1492-1498, 7pgs.

(Continued)

*Primary Examiner* — Jyoti Chawla

(74) *Attorney, Agent, or Firm* — Donald J Silvert; Silvert IP Law

(57) ABSTRACT

A composition and method for supplementing food, nutrition, and diet systems with omega-6 to omega-3 balanced oils comprising a synergistic blend of at least two oils. The composition further comprises a synergistic blend of long-chain omega-3 fatty acids as a means to further increase the nutritional value. The composition provides an effective increase in therapeutic and pharmacological properties in nutrition, and retards the rate of oxidation thereof.

30 Claims, No Drawings

Related U.S. Application Data application No. 16/877,093, filed on May 18, 2020, now Pat. No. 10,918,114, which is a continuation of application No. 14/871,541, filed on Sep. 30, 2015, now Pat. No. 10,653,160, which is a continuation-in-part of application No. 14/288,090, filed on May 27, 2014, now abandoned, which is a continuation of application No. 14/055,619, filed on Oct. 16, 2013, now Pat. No. 10,682,327, which is a continuation of application No. PCT/US2012/033973, filed on Apr. 17, 2012.

(60) Provisional application No. 61/632,827, filed on Apr. 17, 2011.

(56) References Cited

U.S. PATENT DOCUMENTS

| | | | |
|---|---|---|---|
| 5,116,819 | A | 5/1992 | Trimbo et al. |
| 5,166,189 | A | 11/1992 | Trimbo et al. |
| 5,308,832 | A | 5/1994 | Garleb et al. |
| 5,434,183 | A | 7/1995 | Larsson-Backström |
| 5,444,054 | A | 8/1995 | Garleb et al. |
| 5,470,839 | A | 11/1995 | Laughlin et al. |
| 5,549,905 | A | 8/1996 | Mark et al. |
| 5,571,783 | A | 11/1996 | Montagne et al. |
| 5,635,199 | A | 6/1997 | Trimbo et al. |
| 5,661,123 | A | 8/1997 | Stalker et al. |
| 5,670,157 | A | 9/1997 | Trimbo et al. |
| 5,686,429 | A | 11/1997 | Lin et al. |
| 5,714,472 | A | 2/1998 | Gray et al. |
| 5,723,446 | A | 3/1998 | Gray et al. |
| 5,728,678 | A | 3/1998 | Trimbo et al. |
| 5,747,459 | A | 5/1998 | Rowe et al. |
| 5,747,533 | A | 5/1998 | Egberg et al. |
| 5,780,451 | A | 7/1998 | De Michele et al. |
| 5,922,704 | A | 7/1999 | Bland |
| 5,952,295 | A | 9/1999 | Arnaud-Battandier et al. |
| 6,200,950 | B1 | 3/2001 | Mark et al. |
| 8,628,690 | B2 | 1/2014 | Mora-Gutierrez et al. |
| 8,691,293 | B2 | 4/2014 | Gurin |
| 2004/0028622 | A1 | 2/2004 | Gurin |
| 2004/0052920 | A1 | 3/2004 | Koike |
| 2005/0002992 | A1 | 1/2005 | McCleary |
| 2005/0054724 | A1 | 3/2005 | Mustad |
| 2005/0244564 | A1 | 11/2005 | Perlman |
| 2006/0057187 | A1 | 3/2006 | Eskuchen |
| 2007/0196445 | A1 | 8/2007 | Abbruzzese |
| 2007/0196560 | A1 | 8/2007 | Ayoub |
| 2007/0248738 | A1 | 10/2007 | Abril |
| 2009/0110800 | A1 | 4/2009 | Wilkes |
| 2012/0264832 | A1 | 10/2012 | Gurin |

FOREIGN PATENT DOCUMENTS

| | | |
|---|---|---|
| WO | 2005/020698 A1 | 3/2005 |
| WO | 2005/084452 A1 | 9/2005 |
| WO | 2009/102450 A1 | 8/2009 |

OTHER PUBLICATIONS

Singh et al., Randomized, Double-Blind, Placebo-Controlled Trial of Fish Oil and Mustard Oil in Patients with Suspected Acute Myocardial Infarction: The Indian Experiment of Infarct Survival—4, Cardiovascular Drugs and Therapy 1997, vol. 11, 485-491, 8pgs.

Svensson et al., N-3 Fatty Acids as Secondary Prevention against Cardiovascular Events in Patients Who Undergo Chronic Hemodialysis: A Randomized, Placebo-Controlled Intervention Trial, Clin J Am Soc Nephrol 1 (2006), 780-786, 7pgs.

Yokoyama et al., Effects of eicosapentaenoic acid on major coronary events in hypercholesterolaemic patients (JELIS): a randomized open-label, blinded endpoint analysis, The Lancet, Mar. 31, 2007, vol. 369, 1090-1098, 9pgs.

Waitzberg (2005), "Evolution of parenteral lipid emulsions", Clinical Nutritional Supplements 1:5-7 (2005); http://intl.elsevierhealth.com/journals/clnu.

Calder (2006), "Use of fish oil in parenteral nutrition: rationale and reality", Proceedings of the Nutrition Society 65:264-277 (2006); DOI:10.1079/PNS2006500.

Mertes et al. (2006), "Safety and Efficacy of a New Parenteral Lipid Emulsion (SMOFlipid) in Surgical Patients: A Randomized, Double-Blind, Multicenter Study", Ann Nutr Metab 50:253-259 (2006); DOI:10.1159/000091683.

Calder (2007), "Dietary arachidonic acid: harmful, harmless or helpful?", British Journal of Nutrition 98:451-453 (2007); doi: 10.1017/S0007114507761779.

Wanten and Calder (2007), "Immune modulation by parenteral lipid emulsions", Am J Clin Nutr 85:1171-84 (2007); https://academic.oup.com/ajcn/article/85/5/1171/4633073.

Calder (2009), "Rationale for using new lipid emulsions in parenteral nutrition and a review of the trials performed in adults", Proceedings of the Nutrition Society 68:252-260 (2009); doi:10.1017/S0029665109001268.

Jacintho et al. (2009), "Anti-inflammatory effect of parenteral fish oil lipid emulsion on human activated mononuclear leukocytes", Nutrición Hospitalaria 24(3):288-296 (2009); http://www.redalyc.org/articulo.oa?id=309226746005.

Nanhuck et al. (2009), "Effects of lipid emulsions on lipid body formation and eicosanoid production by human peripheral blood mononuclear and polymorphonuclear cells", Clinical Nutrition 28:556-564 (2009); https://doi.org/10.1016/j.clnu.2009.05.008.

Calder et al. (2010), "Lipid emulsions in parenteral nutrition of intensive care patients: current thinking and future directions", Intensive Care Med 36:735-749 (2010); DOI 10.1007/s00134-009-1744-5.

Calder (2010), "Rationale and use of n-3 fatty acids in artificial nutrition", Proceedings of the Nutrition Society 69(4):565-573 (2010); doi:10.1017/S0029665110000157.

Linke et al. (2010), "Does a fish-oil-containing lipid emulsion improve liver function in comparison with a soybean oil lipid emulsion?", Critical Care 14 (Suppl 1):5189 (Abstract #P564) (2010); http://ccforum.com/supplements/14/S1.

Puertollano et al. (2010), "Impact of olive oil-based lipid emulsions in clinical nutrition: Modulation of host defense", Nutritional Therapy and Metabolism (Oct. 2010); https://www.researchgate.net/publication/285989947.

Tomsits et al. (2010), "Safety and Efficacy of a Lipid Emulsion Containing a Mixture of Soybean Oil, Medium-chain Triglycerides, Olive Oil, and Fish Oil: A Randomised, Double-blind Clinical Trial in Premature Infants Requiring Parenteral Nutrition", JPGN 51(4):514-521 (2010); DOI: 10.1097/MPG.0b013e3181de210c.

Janu et al. (2011), "Comparison of Long-Term Stability of Parenteral All-in-One Admixtures Containing New Lipid Emulsions Prepared Under Hospital Pharmacy Conditions", Medicina (Kaunas) 47(6):323-33 (2011).

Mancilla-Ramirez et al. (2011), "Beneficial effects of the n-3 longchain polyunsaturated fatty acids in surgical patients: Updating the evidence", Prostaglandins, Leukotrienes and Essential Fatty Acids 85:261-66 (2011); doi:10.1016/j.plefa.2011.04.012.

Ok et al. (2011), "Lipid Emulsion Reverses Levobupivacaine-induced Responses in Isolated Rat Aortic Vessels", Anesthesiology 114(2):293-301 (2011).

Saayman (2011), "The use of alternative lipid emulsions in paediatric and neonatal parenteral nutrition", S Afr J Clin Nutr 24(3 Suppl):S32-S34 (2011).

Tillman et al. (2011), "Omega-3 Long Chain Polyunsaturated Fatty Acids for Treatment of Parenteral Nutrition-Associated Liver Disease: A Review of the Literature", J Pediatr Pharmacol Ther 16(1):31-38 (2011); www.jppt.org.

Schade et al. (2008), "Inflammatory response in patients requiring parenteral nutrition: comparison of a new fishoil-containing emulsion (SMOF®) versus an olive/soybean oil-based formula", Critical Care 12 (Suppl 2):S56-S57 (Abstract P144) (2008); http://ccforum.com/supplements/12/S2.

Piper et al. (2009), "Hepatocellular integrity after parenteral nutrition: comparison of a fish-oil-containing lipid emulsion with an

(56) References Cited

OTHER PUBLICATIONS olive-soybean oil-based lipid emulsion", European Journal of Anaesthesiology 26:1076-1082 (2009); DOI:10.1097/EJA.0b013e32832e08e0.

Kapoor et al. (2011), "Soy oil based versus alternative lipid emulsions for parenterally fed preterm infants", Cochrane Database of Systematic Reviews, Issue 6. Art. No. CD009172 (2011); DOI: 10.1002/14651858.CD009172.

Amusquivar et al., Influence of Fatty Acid Profile of Total Parenteral Nutrition Emulsions on the Fatty Acid Composition of Different Tissues of Piglets, 43 Lipids 71a-722 (2008).

De Meijer et at., Parenteral Fish Oil as Monotherapy Prevents Essential Fatty Acid Deficiency in Parenteral Nutrition—dependent Patients, 50(2) Journal of Pediatric Gastroenterology and Nutrition 212-218 (2010).

Diamond et al., Changing the Paradigm: Omegaven for the Treatment of Liver Failure in Pediatric Short Bowel Syndrome, 48 Journal of Pediatric Gastroenterology and Nutrition 209-215 (2009).

Diamond et al., The rationale for the use of parenteral omega-3 lipids in children with short bower syndrome and liver disease, 24 Pediatric Surg Int 773-778 (2008).

Foitzik et at., ω-3 Fatty Acid Supplementation Increases Anti-inflammatory Cytokines and Attenuates Systemic Disease Sequelae in Experimental Pancreatitis, 26(6) Journal of Parenteral and Enteral Nutrition 351-56 (2002).

Gura et al., Use of a fish oil-based lipid emulsion to treat essential fatty acid deficiency in a soy allergic patient receiving parenteral nutrition, 24 Clinical Nutrition 839-847 (2005).

Gura et al., Use of a fish oil-based lipid emulsion to treat essential fatty acid deficiency in a soy allergic patient receiving parenteral nutrition, 118(1) Pediatrics e197-e201 (2006).

Le et al., Parenteral fish-oil—based lipid emulsion improves fatty acid profiles and lipids in parenteral nutrition—dependent children, 94 Am J Clin Nutr 749-58 (2011).

Le et al., The essentiality of arachidonic acid and docosahexaenoic acid, 81(2-3) Prostaglandins Leukot Essent Fatty Acids 165-170 (2009).

Lee et at., Current Clinical Applications of Ω-6 and Ω-3 Fatty Acids, 21 Nutr Clin Pract 323-341 (2006).

Liang et al., Impact of postoperative omega-3 fatty acid-supplemented parenteral nutrition on clinical outcomes and immunomodulations in colorectal cancer patients, 14(15) World J Gastroenterol 2434-2439 (2008).

Madsen et al., Effect of Intravenous ω-3 Fatty Acid Infusion and Hemodialysis on Fatty Acid Composition of Free Fatty Acids and Phospholipids in Patients With End-Stage Renal Disease, 35(1) Journal of Parenteral and Enteral Nutrition 97-106 (2011).

Martin and Stapleton, Omega-3 Fatty Acids in Critical Illness, 68(9) Nutr Rev. 531-541 (2010).

Mayer et al., omega-3 vs omega-6 lipid emulsions exert differential influence on neutrophils in septic shock patients: impact on plasma fatty acids and lipid mediator generation, 29 Intensive Care Med 1472-1481 (2003).

Mayser et al., A Double-Blind, Randomized, Placebo-Controlled Trial of n-3 Versus n-6 Fatty Acid—Based Lipid Infusion in Atopic Dermatitis, in 26(3) Journal of Parenteral and Enteral Nutrition 151-158 (2002).

Versleijen et al., Parenteral Lipids Modulate Leukocyte Phenotypes in Whole Blood, Depending on Their Fatty Acid Composition, in 24(5) Clinical Nutrition 822-829 (2005), as publ'd in Michelle Wilhelmina Johanna Versleijen, Complications of Total Parenteral Nutrition: Focus on Fats and Fistulae (2012) (published doctoral dissertation, Radboud Universiteit Nijmegen) (accessible at https://doi.org/10.1016/j.clnu.2005.05.003 and https://www.sciencedirect.com/science/article/pii/S0261561405000762).

Xu et al., An Improved Method for Determining Medium- and Long-Chain FAMEs Using Gas Chromatography, 45 Lipids 199-208 (2010).

Xu, et al., Mechanism Study of Chitosan on Lipid Metabolism in Hyperlipidemic Rats, hereinafter chitosan 1, Asia Pacific Journal of Clinical Nutrition 16 S1 (Apr. 1, 2007) p. 313-317, 5pgs.

KitoZyme launches vegetal chitosan ingredient, Apr. 16, 2010, 3pgs.

Best Food Choices for Omega 3 and Omega 6 and Omega 9 Essential Fatty Acids obtained from http://www.dailyperricone.com/2008/12/best-food-choices-for-omega-3-and-omega-6-and-omega-9, Dec. 3, 2008, 4 pages.

Choe et al., Mechanisms of Antioxidants in the Oxidation of Foods; Comprehensive Reviews in Food Science and Food Safety—vol. 8, 2009—pp. 345-358 (Year: 2009).

International Search Report issued in a corresponding foreign application dated Nov. 29, 2012, 3pgs.

Written Opinion issued in a corresponding foreign application dated Nov. 29, 2012, 3pgs.

International Preliminary Report on Patentability issued in a corresponding foreign application dated Oct. 22, 2013, 1pg.

European Extended Search Report issued in a corresponding foreign application dated Oct. 6, 2014, 6pgs.

McCowen, et al., Effect of a Fish Oil—Containing Beverage on Changes in Plasma Lipid Fatty Acids in Patients With Malabsorption, Nutrition in Clinical Practice, vol. 25, No. 5, pp. 517-523 (Oct. 2010), 7pgs.

Mizock et al., Immunonutrition and critical illness: An update, Nutrition 26, pp. 701-707 (2010), 7pgs.

Van der Meij, et al., Oral Nutritional Supplements Containing (n-3) Polyunsaturated Fatty Acids Affect the Nutritional Status of Patients with Stage III Non-Small Cell Lung Cancer during Multimodality Treatment, The Journal of Nutrition, (2010), 7pgs.

Ross 2006 Pocket Guide, Ross Nutrition (Nov. 2006), 140 pgs.

Abbott Laboratories, Therapeutic Nutrition for People with Cancer, Prosure® Product Monograph (2012), 27 pgs.

Pontes-Arruda et al., Enteral nutrition with eicosapentaenoic acid, γ-linolenic acid and antioxidants in the early treatment of sepsis; results from a multicenter, prospective, randomized, double-blinded, controlled study: the INTERSEPT study (2011), 24 pgs.

Phillippy et al., Antioxidant Functions of Inositol 1,2,3-Trisphosphate and Inositol 1,2,3,6-Tetrakisphosphate; Free Radical Biology & Medicine, vol. 22, No. 6, pp. 939-946, 1997.

University of Maryland Medical Center (2006) "Omega-6 Fatty Acids" Retrieved at http://www.umm.edu/altmed/articles/omega-6-000317.htm on Dec. 2, 2010, 4pgs.

Simopoulos, The Importance of the Ratio of Omega-6/Omega-3 Essential Fatty Acids, Biomed. Pharmacother. 56, 365-379 (Rec'd May 25, 2002), 15pgs.

Pazos et al., Hydroxytyrosol Prevents Oxidative Deterioration in Foodstuff Rich in Fish Lipids, J. Agric. Food Chem. 56, 3334-3340 (2008), 9pgs.

Group, The Health Benefits of Omega 3, 6, 9 Fatty Acids and EPA & DHA? Retrieved at http://www.globalhealingcenter.com/natural-health/benefits-of-omega-3-6-9-fatty-acids/ on Nov. 22, 2010, 10pgs.

Chicago Tribune, Abbott supplement for cancer patients (2003), 2pgs.

Tso et al., Randomized Structed Triglycerides Increase Lymphatic Absorption of Tocopherol and Retinol Compared with the Equivalent Physical Mixture in a Rat Model of Fat Malabsorption, American Society for Nutritional Sciences (2001), 7pgs.

Nestle Nutrition 2006 Product Guide, 84pgs.

Moses et al., Reduced total energy expenditure and physical activity in cachectic patients with pancreatic cancer can be modulated by an energy and protein dense oral supplement enriched with n-3 fatty acids, British Journal of Cancer (2004) 90, 996-1002, 7pgs.

Kenler et al., Early Enteral Feeding in Postsurgical Cancer Patients, Annuals of Surgery, vol. 223, No. 3, 316-333 (1996), 18pgs.

Fearon, et al., Effect of a protein and energy dense n-3 fatty acid enriched oral supplement on loss of weight and lean tissue in cancer cachexia: a randomized double blind trial, Gut 2003, vol. 52, No. 1, 1479-1486, 8pgs.

Barber et al., The effect of an oral nutritional supplement enriched with fish oil on weight-loss in patients with pancreatic cancer, British Journal of Cancer (1999), vol. 81, No. 1, 80-86, 7pgs.

(56) References Cited

OTHER PUBLICATIONS

Bang, et al., Plasma Lipid and Lipoprotein Pattern in Greenlandic West-Coast Eskimos, The Lancet, Jun. 5, 1971, 1143-1146, 5pgs.

Dyerberg et al., Eicosapentaenoic Acid and Prevention of Thrombosis and Atherosclerosis?, The Lancet, Jul. 15, 1978, 116-119, 4pgs.

Fincham et al., Chronic Effects of Fish Oil and a Therapeutic Diet in Nonhuman Primates, Arteriosclerosis and Thrombosis, vol. 11, No. 3, May/Jun. 1991, 719-732, 14pgs.

Harker et al., Interruption of Vascular Thrombus Formation and Vascular Lesion Formation by Dietary n-3 Fatty Acids in Fish Oil in Nonhuman Primates, Circulation, vol. 87, No. 3, Mar. 1993, 1017-1029, 13pgs.

McKenney et al., Prescription omega-3 fatty acids for the treatment of hypertriglyceridemia, Am J Health-Syst Pharm, vol. 64, Mar. 15, 2007, 595-605, 11pgs.

Mori, Omega-3 Fatty Acids and Blood Pressure, Cellular and Molecular Biology, vol. 56, No. 1, 83-92 (2010), 10pgs.

Rich et al., Development of Atherosclerosis in Genetically Hyperlipidemic Rabbits during Chronic Fish-Oil Ingestion, Arteriosclerosis, vol. 9, No. 2, Mar./Apr. 1989, 189-194, 6pgs.

Wall et al., Fatty acids from fish: the anti-inflammatory potential of long-chain omega-3 fatty acids, Nutrition Reviews, vol. 68(5):280-289, 10pgs.

Zhu et al., Regression of Atherosclerosis in Cholesterol-Fed Rabbits: Effects of Fish Oil and Verapamil, JACC vol. 15, No. 1, Jan. 1990, 231-237, 7pgs.

Brouwer et al., Effect of fish oil on ventricular tachyarrhythmia in three studies in patients with implantable cardioverter defibrillators, European Hearth Journal (2009), vol. 30, 820-826, 7pgs.

Bucher et al., N-3 Polyunsaturated Fatty Acids in Coronary Heart Disease: A Meta-analysis of Randomized Controlled Trials, The American Journal of Medicine, Mar. 2002, vol. 112, 298-304, 7pgs.

Hooper et al., Risks and benefits of omega 3 fats for mortality, cardiovascular disease, and cancer: systematic review, BMJ, Mar. 24, 2006, 9pgs.

Marik et al., Omega-3 Dietary Supplements and the Risk of Cardiovascular Events: A Systematic Review, Clin. Cardiol. vol. 32, No. 7, 365-372 (2009), 8pgs.

Wang et al., n-3 fatty acids from fish or fish-oil supplements, but not α-linolenic acid, benefit cardiovascular disease outcomes in primary- and secondary-prevention studies: a systematic review, Am J Clin Nutr 2006, vol. 84, 5-17, 13pgs.

Brouwer et al., Effect of Fish Oil on Ventricular Tachyarrhythmia and Death in Patients with Implantable Cardioverter Defibrillators, JAMA, Jun. 4, 2006, vol. 295, No. 22, 2613-2619, 7pgs.

Einvik et al., A randomized clinical trial on n-3 polyunsaturated fatty acids supplementation and all-cause mortality in elderly men at high cardiovascular risk, The European Society of Cardiology (2010), vol. 15, No. 5, 588-592, 5pgs.

Galan et al., Effects of B vitamins and omega 3 fatty acids on cardiovascular diseases: a randomized placebo controlled trial, BMJ (Nov. 29, 2010), 9pgs.

Garbagnati et al., Is Antioxidant and n-3 Supplementation Able to Improve Functional Status in Poststroke Patients? Results from the Nutristroke Trial, Cerebrovascular Diseases (2009), 375-383, 10pgs.

Kromhout et al., n-3 Fatty Acids and Cardiovascular Events after Myocardial Infarction, The New England Journal of Medicine (2010), vol. 363, No. 21, 2015-2026, 12pgs.

Leaf et al., Prevention of Fatal Arrhythmias in High-Risk Subjects by Fish Oil n-3 Fatty Acid Intake, Circulation (Nov. 1, 2005), 2762-2768, 7pgs.

Leng et al., Randomized controlled trial of gamma-linolenic acid and eicosapentaenoic acid in peripheral arterial disease, Clinical Nutrition (1998), vol. 17, No. 6, 265-271, 7pgs.

Nilsen et al., Effects of a high-dos concentrate of n-3 fatty acids or corn oil introduced early after an acute myocardial infarction on serum triacylglycerol and HDL cholesterol, Am J Clin Nutr 2001, vol. 74, 50-56, 7pgs.

Raitt et al., Fish Oil Supplementation and Risk of Ventricular Tachycardia and Ventricular Fibrillation in Patients with Implantable Defibrillators, JAMA (Jun. 15, 2005), vol. 293, No. 23, 2884-2891, 8pgs.

Rauch et al., OMEGA, a Randomized, Placebo-Controlled Trial to Test the Effect of Highly Purified Omega-3 Fatty Acids on Top of Modern Guideline-Adjusted Therapy After Myocardial Infarction, Circulation (Nov. 23, 2010), 2152-2159, 8pgs.

PRODUCTS HAVING HIGH EFFICACY OMEGA-6/OMEGA-3 BALANCED POLYUNSATURATED FATTY ACIDS

CROSS REFERENCE TO RELATED APPLICATIONS

This is a continuation of U.S. application Ser. No. 17/860,066, filed Jul. 7, 2022, which is a continuation of U.S. application Ser. No. 17/497,843, filed Oct. 8, 2021, issued as U.S. Pat. No. 11,490,630, which is a continuation of U.S. application Ser. No. 17/175,457, filed Feb. 12, 2021; which is a continuation-in-part of U.S. application Ser. No. 16/877,093, filed May 18, 2020; which is a continuation of U.S. application Ser. No. 14/871,541, filed Sep. 30, 2015, issued as U.S. Pat. No. 10,653,160; which is a continuation-in-part of U.S. application Ser. No. 14/288,090, filed May 27, 2014; which is a continuation of U.S. application Ser. No. 14/055,619 filed on Oct. 16, 2013, issued as U.S. Pat. No. 10,682,327; which is a continuation of international application PCT/US2012/033973, international filing date Apr. 17, 2012; all of which claim the benefit of U.S. Provisional Application 61/632,827, filed Apr. 17, 2011. All patent applications and patents recited herein above are incorporated by reference in their entireties.

FIELD OF THE INVENTION

The present invention relates generally to the field of food science, more particularly to formulations of enhanced nutrition relating to nutraceuticals, pharmaceuticals, foods, and functional foods, and to the significant reduction in oxidation for such products.

BACKGROUND OF THE INVENTION

Dietary fish oil preparations containing omega-3 polyunsaturated fatty acids have been reported to have a number of health-inducing characteristics. As asserted in various publications, dietary fish oil preparations are believed to promote more healthful levels of triglyceride, HDL cholesterol, homocysteine, and blood pressure as well as enhance the effectiveness of statin drugs used to treat cholesterol levels. See, e.g., U.S. Pat. Nos. 3,082,228, 4,097,602, and 5,698,594; British Patent 2,197,199; and International Patent Publication WO 87/02247.

Fatty acids come in various categories of carbon chain length, meaning the number of carbon atoms in the aliphatic tail that are linked together per molecule. The "aliphatic tail" is composed of a series of carbon atoms, as noted, from the terminal methyl group (i.e., —CH3) to the carboxyl group (—COOH) at the other end of the fatty acid; the carbon of the carboxyl group is not included in the considered number of carbons of the aliphatic chain.

Short-chain fatty acids have fewer than 20 carbon atoms in their aliphatic tails, such as alpha-linolenic acid ("ALA"). Long-chain fatty acids have at least 20 carbons, such as docosahexaenoic acid ("DHA") and eicosapentaenoic acid ("EPA").

Fatty acids can be "saturated," meaning that each carbon atom of the aliphatic tail is linked by C—C single bonds, the lowest energy state of carbon-to-carbon bonds that are most difficult to digest. "Unsaturated" fatty acids, however, include at least one double bond between adjacent carbon atoms of the aliphatic tail, which affords more energy to such bonds and renders the unsaturated fatty acid more readily digested; as suggested by the prefix, "poly-", polyunsaturated fatty acids ("PUFAs") have multiple double-bonds and are generally known to be more healthful.

Some fatty acids found in nature are "essential" in that humans cannot manufacture them and therefore must ingest them because they are needed for certain cellular functions. Notable among the essential polyunsaturated fatty acids are the omega-3 category and the omega-6 category, so-named for the position of a first double bond after the third carbon or the sixth carbon from the methyl terminal.

Omega-3 fatty acids are believed to be the primary source of the above-mentioned good effects of dietary fish oil preparations. Such omega-3 fatty acids are found naturally in the oil of cold-water fish, such as mackerel, salmon, sardines, anchovies and tuna. Omega-3 fatty acids are also found naturally in extracted alpha-linolenic acid ("ALA") from plants, such as flaxseed and canola (rapeseed). However, the human body converts ALA to the healthful DHA and EPA very inefficiently, less than 1 percent by some estimates. (Andrea Klausner, Berkeley Wellness, *Not All Omega-3s are the Same* (1 Apr. 2011), available at https://www.berkeleywellness.com/healthy-eating/food/article/not-all-omega-3s-are-same).

Omega-6 fatty acids are plentiful in most readily available oils that are part of the human diet, namely vegetable oil extracted from any of various commercially raised oil seeds, e.g., corn, soy, canola, flax. The ratios of omega-6 to omega-3 fatty acids in some common vegetable oils are: canola 2:1, soybean 7:1, olive 3-13:1, sunflower (no omega-3), flax 1:3, cottonseed (almost no omega-3), peanut (no omega-3), grapeseed oil (almost no omega-3) and corn oil 46:1 ratio of omega-6 to omega-3.

Currently, western diets generally contain a ratio of omega-6 to omega-3 fatty acids of more than 15:1. This change in fatty acid consumption toward excessive intakes of omega-6 polyunsaturated fatty acids resulting in a very high omega-6 to omega-3 ratio has been implicated as the source of or a contributor to a variety of diseases, including cardiovascular, cancer, inflammatory, and autoimmune diseases.

There is a growing body of scientific evidence indicating the health benefits of a lower omega-6 to omega-3 fatty acid ratio, including improved immune function as well as cardiovascular, bone, and mental health benefits. In particular, studies suggest that an omega-6 to omega-3 ratio of less than 6:1 may be associated with health benefits, whereas a ratio of 10:1 or greater may be associated with adverse health effects. Various federal agencies and scientific organizations are placing an increased emphasis on increasing omega-3 fats in the diet.

However, developing foods enriched with the healthful omega-3 polyunsaturated fatty acids ("PUFAs") is a major challenge. (Charlotte Jacobsen, *Challenges when developing omega-3 enriched foods,* 17(4) OCL 251 (15 Jul. 2010), available at https://doi.org/10.1051/ocl.2010.0327). Due to their polyunsaturated nature, long-chain omega-3 PUFAs such as DHA and EPA are highly susceptible to lipid oxidation which leads to the formation of undesirable fishy and rancid off-flavors. (Id.). Due to this propensity towards lipid oxidation, the industry standard of EPA and DHA per serving seldom exceeds 32 mg per serving. Moreover, due to that propensity to oxidization by EPA and DHA, the shelf life of products containing even low levels of such omega-3 PUFAs are generally limited to no more than a few months, thus lessening the product's shelf life relative to the same product without the omega-3 addition.

The present invention attempts to solve the problems caused by an imbalance of healthful fatty acids in the modern diet while addressing the undesirable effects of lipid oxidation. In particular, the present invention solves the problem of limited shelf life for storage of oil blends containing high amounts of omega-3 PUFAs and, as well, that of end products comprising high levels of omega-3 PUFAs. Such products can ameliorate today's largely unhealthy diet that contains an overwhelmingly high proportion of omega-6 PUFAs and is believed to be behind a broad swath of contemporary health issues.

SUMMARY OF THE INVENTION

It is an object of the present invention to maximize the bioavailability and serving size of certain edible oils, such as omega-3 long-chain PUFAs, by preparing foods that include high levels of omega-3 PUFAs where adverse enzymatic and oxidation reactions from so manufacturing to consumption of the products are minimized.

The omega-6/omega-3 balanced polyunsaturated fatty acid blend of the present invention ("Omega-6:3 PUFA Blend") comprises a blend or combination of edible oils that can be included in foods, nutraceuticals, pharmaceuticals (collectively, "Omega-6:3 Products"). The Omega-6:3 PUFA Blend, or the oils with which the blend is made, can be included with base compositions for individual Omega-6:3 Products. Essentially, such Omega-6:3 Products result from the addition thereto of the individual component oils of the Omega-6:3 PUFA Blend, or one or more of the component oils can be combined prior to addition to the base composition that, once added, form the Omega-6:3 Product. In other words, how the ratios of fatty acids disclosed herein that have been found to retard oxidation of omega-3 PUFAs are introduced into the Omega-6:3 Product is not material to this invention, i.e., they can be set forth in a mixture of the oils prior to addition to a base composition or the oils can be added individually to the base composition, or a portion of the oil to be added to the base composition can be mixed together prior to addition to the base composition, and additional oil or oils can be added thereafter to adjust the Omega-6:3 Product to the inventive ratio(s) of fatty acids.

In this disclosure, particularly in the examples describing manufacturing protocols for making various Omega-6:3 Products, applicants have described the creation of a mixture of omega-3 and omega-6 fatty acids, often in combination with an antioxidant, that is called the Omega-6:3 PUFA Blend. It can be stored in excess of a year at refrigerator or freezer temperatures. And, it can be used to add the inventive ratio of fatty acids to the various Omega-6:3 Products by adding it to a base composition, as appropriate. Together, the identified fatty acids plus the base composition forms a particular Omega-6:3 Product of the present invention. These descriptions present but one protocol for making the various Omega-6:3 Products. By no means are the examples of manufacturing protocols set forth herein intended to limit how Omega-6:3 Products are manufactured.

Any of the protocols set forth herein below can be readily altered by one of ordinary skill in the art to add the individual components of the Omega-6:3 PUFA Blend, or its component oils added individually or by subsets, to a base composition either individually, in concert or in sequence. Accordingly, some portion of the oils can be added from pre-mixed sources and individual oils added as well, ultimately resulting in the inventive ratio of the indicated oils. The sequence of or method used for adding the components of the Omega-6:3 PUFA Blend, altogether or individually in any order is immaterial to the present invention. What is material to the present invention is that the end Omega-6:3 Product must have the identified ratios of fatty acids resulting from the specified combination of oils as set forth for a particular Omega-6:3 PUFA Blend, with or without the antioxidant.

One exemplary embodiment is the use of the Omega-6:3 PUFA Blend, or its component oils, in an enhanced food, generically referred to as a "functional food," such as a drink or a mayonnaise or a sauce enhanced by the oils of the Omega-6:3 PUFA Blend contained therein. The oils of the Omega-6:3 PUFA Blend retain oxidation resistance and stability when stored together as the blend having the disclosed fatty acid ratios or after incorporation into an Omega-6:3 Product, in contrast to oil blends that are outside of the inventive ratios of the Omega-6:3 PUFA Blend.

As utilized in the present application, the Omega-6:3 PUFA Blend, or the oils thereof if added by subsets, maintains an omega-6 to omega-3 ratio of about 5:1 or better (meaning that the omega-6 component occupies a lesser amount of the omega-6 to omega-3 ratio, such as about 4:1, about 3:1, about 2:1, about 1:1, etc.).

The Omega-6:3 PUFA Blend also maintains a ratio of short-chain omega-3 PUFAs to long-chain omega-3 PUFAs from about 5:1 or better (meaning that the short-chain omega-3 component occupies a lesser amount of said ratio, such as about 4:1, about 3:1, about 2:1, etc.). In certain embodiments, Omega-6:3 PUFA Blend, or the oils thereof added by subsets, is included in the end product so as to deliver at least about 50 mg of combined DHA and/or EPA per standard serving of the end product into which the Omega-6:3 PUFA Blend, or the oils thereof, is incorporated.

In certain embodiments of the present invention, there are pairings of the ratios of (i) omega-6 to omega-3 PUFAs and (ii) short-chain omega-3 to long-chain omega-3 PUFAs. For example, in one embodiment, the respective paired ratios are: (i) about 0.1:1 to about 2:1 for the omega-6 to omega-3 PUFAs, and (ii) about 0.05:1 to about 2:1 for the short-chain to long-chain omega-3 PUFAs. In a second embodiment, the respective paired ratios are: (i) about 0.5:1 to about 2:1 for the omega-6 to omega-3 PUFAs, and (ii) about 0.01:1 to about 1:1 for the short-chain to long-chain omega-3 PUFAs. And, in a third embodiment, the respective paired ratios are: (i) about 1:1 to about 2:1 for the omega-6 to omega-3 PUFAs, and (ii) about 0.1:1 to about 1:1 for the short-chain to long-chain omega-3 PUFAs. These paired ratios are reflected in the following chart:

|  | (i) omega-6 to omega-3 fatty acids, by weight | (ii) short-chain omega-3 to long-chain omega-3 PUFAs, by weight |
| --- | --- | --- |
| 1st Pair of Ratio Ranges | about 0.1:1 to about 2:1 | about 0.05:1 to about 2:1 |
| 2nd Pair of Ratio Ranges | about 0.5:1 to about 2:1 | about 0.01:1 to about 1:1 |
| 3rd Pair of Ratio Ranges | about 1:1 to about 2:1 | about 0.1:1 to about 1:1 |

The Omega-6:3 PUFA Blend can also include various additives to help improve oxidation resistance and stability. These additives may include antioxidants, phytosterols, and the like.

Definitions

The following definitions relate to terms usefully employed in describing the present invention. If any of these terms are differently defined elsewhere in this disclosure or in this application's course of prosecution, it is applicants' intention to rely on the definitions set forth in this section and they should govern.

The term "polyunsaturated fatty acids" is abbreviated to the acronym PUFA.

The term "long-chain omega-3 PUFA" means DHA or EPA. DHA is docosahexaenoic acid 22:6 (n-3), and EPA is eicosapentaenoic acid 20:5 (n-3).

The term "short-chain omega-3 PUFA" means ALA. ALA is alpha-linolenic acid, 18:3 (n-3).

The term "Omega-6:3 PUFA Blend" means a blend of oils with an aggregate omega-6 to omega-3 fatty acid ratio between about 0.01:1 and about 5:1, and a short-chain omega-3 to long-chain omega-3 fatty acid ratio between about 0.01:1 and about 5:1.

The term "Omega-6:3 Product" means any food, nutritional preparation, drink, nutraceutical, and pharmaceutical that includes the ratios of (i) omega-6 to omega-3 fatty acids and (ii) short-chain omega-3 to long-chain omega-3 fatty acids, as disclosed and claimed herein. Such Omega-6:3 Products can be manufactured from a base composition to which the Omega-6:3 PUFA Blend, or its component oils, is added. Omega-6:3 Products include, but are not limited to: mayonnaise or mayonnaise-like foods, salad dressings ranch, Caesar, thousand island, blue cheese, Italian, lite Italian, three pepper ranch, balsamic vinaigrette, raspberry vinaigrette, and French, French dressing-like foods, peanut butter or peanut butter-like foods, nut butter, tomato-based pasta sauce, alfredo sauce, and basil pesto sauce; and drinks, including, without limitation intended, fruit juice, dairy or plant-based smoothies, coffee creamer, flavored and unflavored beverages, nutritional shakes, clinical nutrition drinks, juices, dairy milk or plant-based milk, nut-based milk, kefir drinks, and sports drinks. The oils included in an Omega-6:3 Product may be introduced into the base composition of the product under manufacture via pre-mixed compositions of oils or subsets thereof added in concert or sequentially, in any order. An Omega-6:3 Product may also include an antioxidant that is added prior to, in combination with, or after the oils are added. An Omega-6:3 Product can also comprise only the Omega-6:3 PUFA Blend, for example, as a container thereof sold to manufacturers of other Omega-6:3 Products or consumers seeking a healthful source of edible oil, including olive oil and combinations of olive and other edible oils, or a packaged aliquot of said blend used as a nutraceutical, as yet another example.

The term "shelf life," hyphenated or not, as used herein, means the length of time that a food product can be stored under standard conditions before its quality deteriorates to a point where it is no longer suitable for consumption. Different food products naturally have different shelf lives due to the inherent deterioration characteristics of their respective components. Standard bread products, for example, will deteriorate within just two weeks, whereas a standard tomato-based pasta sauce will not deteriorate for at least 12-18 months. which is before the omega-3 fatty acids will oxidize to a rancid state. Other foods have naturally longer shelf lives based on their non-omega-3 components, such as a tomato-based pasta sauce that can remain suitable for consumption for at least 12-18 months. But, inclusion of healthful, high levels of omega-3 fatty acids to a level of 50 mg per serving, or greater, will lessen the shelf life of the tomato-based pasta sauce to about two to three months unless frozen or made in conformity with the present invention with regard to the ratios of the omega fatty acids as disclosed herein.

The term "base composition" means the combined set of ingredients for a particular Omega-6:3 Product to which is added the Omega-6:3 PUFA Blend, or subsets of component oils thereof, in the manufacture of said Omega-6:3 Product.

The term "medium chain triglycerides" ("MCTs") means medium chain (6 to 12 carbons) fatty acid esters of glycerol.

The term "functional food" means a modified food that improves health or well-being by providing benefit beyond that of the traditional nutrients it contains. As noted above, a functional food can be enhanced in its health-improving or -promoting characteristics by the inclusion of the oils of an Omega-6:3 PUFA Blend thereby increasing the amount of long-chain omega-3 PUFAs that are delivered per serving.

The term "nutraceutical" means a product isolated or purified from foods that is generally sold in medicinal forms not usually associated with food. As an example, the oils of the Omega-6:3 PUFA Blend, if encapsulated in a pill, would be a nutraceutical.

The term "Omega-6:3 Product" means any food, beverage, nutraceutical, or pharmaceutical that have an omega-6 to omega-3 fatty acid ratio as disclosed herein. Omega-6:3 Products include, without limitation intended, a functional food, nutritional shake, surgical shake, and the like.

DETAILED DESCRIPTION OF THE INVENTION

It is an object of the present invention to maximize the bioavailability and serving size of omega-3 long-chain polyunsaturated fatty acids ("PUFAs") by preparing Omega-6:3 Products in which adverse enzymatic and oxidation reactions are minimized from manufacturing to consumption.

In one embodiment of the invention, a functional food product is made by use of the oils that form the Omega-6:3 PUFA Blend, containing at least 50 mg of long-chain omega-3 PUFAs per serving. The Omega-6:3 PUFA Blends can also be incorporated into foods, pharmaceuticals, nutraceuticals, and/or the like.

In some embodiments, the oils of the Omega-6:3 PUFA Blend is incorporated into a composition for production of a food product. Particular, non-limiting examples of food products include mayonnaise or mayonnaise-like foods, salad dressing or salad dressing-like foods (including Ranch-style and Caesar), French and French-style dressings, pasta sauce, alfredo sauce, peanut butter and peanut butter-like foods, nut butter, and the like.

Oils Used in Making Oil Blends or Omega-6:3 Products

High Oleic Peanut Oil, hereinafter referred to as "Peanut-Hi9," includes linoleic acid at a concentration that is less than about 3.5%, or less than about 3.2%, or less than about 3%. Or less than about 2.9% on a weight basis, depending for which embodiment the Peanut-Hi9 is employed. The oleic acid component generally occupies greater than about 75% or greater than about 79% on a weight basis of the Peanut-Hi9. In other embodiments, oleic acid occupies about 75% or about 79% of the Peanut-Hi9.

High Oleic *Moringa oleifera* seed oil, hereinafter referred to as "MO-Hi," has linoleic composition greater than about 3%, greater than about 2%, or greater than about 1% on a weight basis. In other embodiments, the oleic occupies about 70% or about 74% of the MO-Hi.

High linolenic Flax Oil, hereinafter referred to as "Flax-Hi3," has a linolenic to linoleic ratio that is about 6:1 or greater, or about 6.2:1 or greater, or about 6.4:1 or greater. Referring only to the linolenic content, the Flax-Hi3 is at least about 65% linolenic, or at least about 68% linolenic, or at least about 72% linolenic, on a weight basis.

High oleic oils, hereinafter referred to as "Hi-9," from various producers are known in the art and may be utilized in the present invention. One particular high oleic oil, Plenish® high oleic oil, is a product of Pioneer Hi-Bred International, Inc., a division of DuPont. The Plenish® high oleic oil is a soybean oil that has at least about 75% oleic (18:1) on a weight basis, less than about 10% linoleic (18:2) on a weight basis, and less than about 3% linolenic (18:3) on a weight basis. In other embodiments, the oleic occupies about 75%, the linoleic occupies about 10%, and the linolenic occupies about 3% of the Hi-9 on a weight basis.

Omega-3 enriched oils (e.g., fish oil, concentrated fish oil, microalgae oil (such as that available from Martek Biosciences Corporation, a division of DSM Nutritional Products AG, etc.)) having a long-chain omega-3 PUFA (DHA or EPA) content of at least about 20% on a weight basis may be utilized in the present invention. In some embodiments, omega-3 enriched oils having a long-chain PUFA content approaching about 100% on a weight basis may be utilized. In other embodiments, omega-3 enriched oils or oil blends having a long-chain omega-3 PUFA content of about 25%, of about 30%, of about 40%, of about 50%, of about 60%, of about 70%, of about 80%, or of about 90% are employed in the products and methods of the present invention.

The products and methods of the present invention do not incorporate any or minimally incorporate arachidonic acid, a long-chain omega-6 polyunsaturated fat (20:4 (n-6)). An oil employed in the context of the present invention may contain trace amounts of arachidonic acid; but, in one embodiment, no end product or oil component of an end product manufactured in accordance with the present invention will include arachidonic acid at a level greater than about 20% on a weight basis relative to the total weight of omega-6 fatty acid. In another embodiment, the arachidonic acid present in an end product or oil component of an end product of the present invention will not exceed in weight about 10% of the total omega-6 fatty acid present. In yet another embodiment, the arachidonic acid present in an end product or oil component of an end product of the present invention will not exceed in weight about 5% of the total omega-6 fatty acid present.

Specific Omega-6:3 PUFA Blends

In a first embodiment, the Omega-6:3 PUFA Blend is a blend of at least two oils comprised of a first oil derived from flax seed and a second oil derived from a high oleic producing soybean. The oil derived from flax seed is Flax-Hi3, where the Flax-Hi3 is less than about 8%, and in some embodiments less than about 7.5%, and in yet another embodiment, less than about 7.4% by weight basis of the Omega-6:3 PUFA Blend of the first embodiment. The second oil, Hi-9, occupies at least about 91% by weight basis of the first embodiment of the Omega-6:3 PUFA Blend. Accordingly, the Omega-6:3 PUFA Blend of the first embodiment has an oleic weight composition of at least about 60%, or at least about 63%, or at least about 64%. In another embodiment, the oil blend that combines a flax seed oil and a high oleic oil has an oleic weight composition that is about 60%, or about 63%, or about 64.5%.

In a second embodiment, the Omega-6:3 PUFA Blend is a blend of at least two oils comprised of a first oil derived from flax seed and a second oil derived from peanuts. The flax seed oil is the aforementioned Flax-Hi3, where the Flax-Hi3 has an approximately equal balance of omega-6 and omega-3 fatty acids (i.e., a ratio of 1:1), or has a ratio of omega-6 to omega-3 fatty acids where the omega-3 portion is greater than the omega-6 portion. The oil blend composition of the second embodiment has less than about 6% Flax-Hi3, or less than about 5% Flax-Hi3, or less than about 4% Flax-Hi3 by weight, combined with the Peanut-Hi9 that occupies at least about 95% of the oil blend by weight, such that the second embodiment oil blend has an oleic weight composition that is at least about 65%, or at least about 70%, or at least about 74%.

In a third embodiment, the Omega-6:3 PUFA Blend includes an oil having a balanced ratio of omega-6:omega-3 fatty acids that has a ratio of 1:1 or lower. This Omega-6:3 PUFA Blend comprises a first oil derived from flax seed, namely the aforementioned Flax-Hi3, and a second oil derived from the seed of a tree or bush known as *Moringa oleifera*, namely the aforementioned MO-Hi. The Flax-Hi3 component occupies on a weight basis less than about 2% in one implementation, less than about 1.5% in a second implementation, or less than about 1% in a third implementation of this Omega-6:3 PUFA Blend. The second oil of MO-Hi occupies on a weight basis at least about 98% such that the blended third embodiment oil has an oleic weight basis of at least about 65% in one implementation, or at least about 70% in a second implementation, or at least about 72% in a third implementation.

One embodiment of the Omega-6:3 PUFA Blend is a concentrate comprised of multiple oils resulting in an omega-6 to omega-3 ratio from about 0.01:1 to about 4:1. In another embodiment, the ratio is between about 0.01:1 to about 1:1; in a third embodiment, the ratio is between about 0.5:1 to about 1:1; in a fourth embodiment, the ratio is between about 1:1 to about 4:1; in a fifth embodiment, the ratio is between about 1:1 to about 3:1; in a sixth embodiment, the ratio is between about 2:1 to about 3:1; in a seventh embodiment, the ratio is between about 2:1 to about 4:1; in an eighth embodiment, the ratio is between about 3:1 to about 4:1. Generally speaking, in view of the generally abundant sources of omega-6 PUFAs, the present invention emphasizes embodiments that have heightened omega-3 concentrations relative to the omega-6 concentration in a given Omega-6:3 PUFA Blend or prepared food.

In the various Omega-6:3 PUFA Blends set forth herein, the second oil commonly has an omega-9 to omega-6 ratio from about 5:1 to about 20:1, or from about 5:1 to about 15:1, or from about 5:1 to about 10:1, or from about 10:1 to about 20:1, or from about 15:1 to about 20:1. The second oil is blended with an omega-3 enriched oil (e.g., fish oil, concentrate fish oil, microalgae oil, etc.) having, on a weight basis, a long-chain omega-3 PUFA content of at least 20%, or at least 25%, or at least 30%, or at least 40%, or at least 50%, or at least 60%, or at least 70%, or at least 80%, or at least 90%, or about 99% on a weight basis. In one embodiment, the second oil has less than about 5% or less than about 4%, or is about 3% or 2%, by weight of linolenic acid, in order to minimize oxidation between the time of manufacturing and the time of consumption. Linolenic acid, which is a short-chain omega-3 PUFA, does not have a competing interaction with long-chain omega-3 PUFAs, but will adversely impact shelf life.

In another embodiment, the second oil also has an omega-6 to omega-3 ratio from about 0.01:1 to about 4:1, or from about 0.01:1 to about 1:1; or from about 0.5:1 to about 1:1; or from about 1:1 to about 4:1; or from about 1:1 to about 3:1; or from about 2:1 to about 3:1; or from about 2:1 to about 4:1; or from about 3:1 to about 4:1; or from about 0.01:1 to about 0.2:1, or from about 0.01:1 to about 0.25:1. Additionally, in yet other embodiments, the second oil has an omega-6 to omega-3 ratio between about 0.01 to about 0.2; and an omega-9 to omega-6 ratio of at least about 5:1, i.e., for example, from about 50:1 to about 5:1, or from about 20:1 to about 5:1, or from about 50:1 to about 20:1.

In another embodiment, the second oil has an omega-6 to omega-3 ratio between about 0.01:1 and about 3:1; in a third embodiment, the ratio is between about 0.01:1 and about 1:1; in a fourth embodiment, the ratio is between about 1:1 and about 2:1; in a fifth embodiment, the ratio is between about 2:1 and about 3:1; in a sixth embodiment, the ratio is between about 1:1 and about 3:1; in a seventh embodiment, the ratio is between about 0.01:1 and about 2:1; in an eighth embodiment, the ratio is between about 0.01:1 and about 0.5:1.

In yet another embodiment, the second oil has an omega-9 to omega-6 ratio between about 5:1 and about 9:1; in a third embodiment, the ratio is between about 9:1 and about 25:1; in a fourth embodiment, the ratio is between about 50:1 and about 25:1; in a fifth embodiment, the ratio is between about 9:1 and about 25:1; in a sixth embodiment, the ratio is between about 40:1 and about 30:1; in a seventh embodiment, the ratio is between about 50:1 and about 40:1; and in an eighth embodiment, the ratio is between about 1:1 and about 5:1.

Another embodiment of the Omega-6:3 PUFA Blend is a concentrate comprised of multiple oils having an aggregate omega-9 to omega-3 ratio from greater than 4:1 to about 1:1, with at least 20% of the oil concentrate on a weight basis being long-chain omega-3 PUFAs (i.e., DHA or EPA). The Omega-6:3 PUFA Blend is often utilized in a range of food systems, where it is desirable to maximize the omega-9 content and, in consequence, lessen the omega-6 content.

In one embodiment of the present invention, omega-9 to omega-3 long-chain PUFAs ratio of the second oil is from less than about 500:1 to about 1:1. In a second embodiment, the second oil has an omega-9 to omega-3 long-chain PUFA ratio between about 1:1 and about 100:1; in a third embodiment, the ratio is between about 1:1 and about 50:1; in a fourth embodiment, the ratio is between about 100:1 and about 500:1; in a fifth embodiment, the ratio is between about 1:1 and about 200:1; in a sixth embodiment, the ratio is between about 200:1 and about 400:1; in a seventh embodiment, the ratio is between about 1:1 and about 300:1; in an eighth embodiment, the ratio is between about 50:1 and about 300:1; and in a ninth embodiment, the ratio is between about 50:1 and about 200:1.

In another embodiment, the second oil has a composition of at least about 70% oleic acid. Another embodiment of the second oil consistent with this embodiment contains at least about 70% oleic acid, less than about 4% linolenic acid, and less than about 4% linoleic acid.

The presence of omega-3 fatty acid in an oil blend tends to minimize the stability of the oil blend due to the propensity of the omega-3 fatty acids to oxidize and turn rancid. Accordingly, a balanced omega-6 to omega-3 ratio of fatty acids with reasonable stability characteristics can result in an Omega-6:3 PUFA Blend that contains less than about 6% by weight of linolenic acid and where the omega-6 to omega-3 ratio is from about 0.5:1 to about 1:1. In another embodiment, the omega-6 to omega-3 ratio is between about 0.01:1 and about 0.5:1; in a third embodiment, the ratio is between about 0.01:1 and about 1:1; in a fourth embodiment, the ratio is between about 0.5:1 and about 2:1; in a fifth embodiment, the ratio is between about 0.01:1 and about 2:1; in a sixth embodiment, the ratio is between about 0.5:1 and about 0.7:1; and in a seventh embodiment, the ratio is between about 0.7:1 and about 1:1. In another embodiment, the Omega-6:3 PUFA Blend contains less than about 4% linolenic car less than about 2% linolenic, on a weight basis.

In another embodiment of the present invention, a balanced omega-6 to omega-3 ratio is achieved by maximizing the weight percentage of oleic acid, wherein, for example, the oleic weight percentage basis is greater than about 60%. In other embodiments, the oleic weight basis is greater than about 65% or greater than about 70%.

In yet another embodiment, the second oil has an omega-9 to omega-6 ratio greater than about 9:1, or greater than about 25:1. In this embodiment, the second oil has an omega-9 to omega-6 ratio between about 5:1 and about 9:1; or between about 9:1 and about 25:1; or between about 50:1 and about 25:1; or between about 9:1 and about 25:1; or between about 40:1 and about 30:1; or between about 50:1 and about 40:1; or between about 1:1 and about 5:1. The first oil has a linolenic weight percentage greater than about 70%.

Specific exemplary formulations of the Omega-6:3 PUFA Blend include at least a first oil and a second oil resulting in a blended oil having an omega-6 to omega-3 ratio from about 0.01:1 to about 4:1, and having a blended composition of: 1) at least about 60% oleic acid, at least about 0.5% linolenic acid, and at most about 8% linoleic acid; or 2) at least about 65% oleic acid, at most about 8% linolenic acid, and at most about 4% linoleic acid; or 3) at least about 65% oleic acid, at most about 4% linolenic acid, and at most about 2% linoleic acid. In another exemplar embodiment, the ratio of omega-6 to omega-3 is between about 0.01:1 and about 1:1; in a third embodiment, the ratio is between about 0.5:1 and about 1:1; in a fourth embodiment, the ratio is between about 1:1 and about 4:1; in a fifth embodiment, the ratio is between about 1:1 and about 3:1; in a sixth embodiment, the ratio is between about 2:1 and about 3:1; in a seventh embodiment, the ratio is between about 2:1 and about 4:1; in an eighth embodiment, the ratio is between about 3:1 and about 4:1.

In yet another embodiment, the Omega-6:3 PUFA Blend contains a third oil having an omega-3 long-chain PUFA weight basis of at least about 20 percent to about 100 percent; alternative compositions of the third oil include omega-3 long-chain PUFA weight basis of at least about 25%, or at least about 30%, or at least about 40%, or at least about 50%, or at least about 60%, or at least about 70%, or at least about 80%, or at least about 90%, or about 99%. The oil of this embodiment maximizes the weight percent of omega-3 long-chain PUFAs, resulting in a blend high in DHA and EPA and low in omega-6 fatty acids.

The Omega-6:3 PUFA Blend, or the component oils thereof, can be added to a wide range of consumer products, including food, beverage, nutritional supplement, or pharmaceutical products, which are collectively referred to as Omega-6:3 Products. In some embodiments, the Omega-6:3 Products can have a long-chain omega-3 (i.e., DHA and EPA) dosage of greater than 50 mg per standard serving. The Omega-6:3 PUFA Blend formulations, or oils thereof, notably for food products that are rich in oil (e.g., mayonnaise, salad dressings, peanut butter, etc.), commonly use oils having an aggregate omega-6 to linolenic ratio of less than about 3:1, an aggregate omega-9 to linolenic ratio of less than about 10:1, and an aggregate omega-6 to long-chain omega-3 PUFAs ratio of less than about 0.5:1.

As noted herein above, these Omega-6:3 Products having the identified ratios of certain PUFAs can be manufactured by the addition of the pre-mixed Omega-6:3 PUFA Blend or addition of the component oils individually, thus resulting in the identified PUFA ratios, to the mixture of ingredients, or a combination of some pre-mixed oils and others, or additional oil, added separately. In other words, the combination of edible oils, with or without an antioxidant, is included in an Omega-6:3 Product. The oils and antioxidant are added to the base composition of said product as a single combination of edible oils and antioxidant, or one or more subsets of said combination.

Antioxidants

Antioxidants are often added to fat-containing foods to delay the onset or slow the development of rancidity due to oxidation. Natural antioxidants include polyphenols (for instance flavonoids), ascorbic acid (vitamin C), and mixed tocopherols (vitamin E). Synthetic antioxidants include butylated hydroxyanisole ("BHA"), butylated hydroxytoluene ("BHT"), tert-butylhydroquinone ("TBHQ"), propyl gallate, and ethoxyquin. The natural antioxidants tend to be short-lived, so synthetic antioxidants are used when a longer shelf life is wanted. The effectiveness of water-soluble antioxidants is limited in preventing direct oxidation within fats, but is valuable in intercepting free radicals that travel through the watery parts of foods.

Another embodiment of the Omega-6:3 PUFA Blend incorporates at least 2% of pineapple juice on a weight basis to the omega-3 long-chain PUFA weight. One formulation further comprises a sinapyl compound including the sinapyl compound as isolated from pineapple juice. In many embodiments of the present invention, the oil blend formulation does not include pineapple juice. One alternative is to include a sinapyl compound as isolated from pineapple juice into the Omega-6:3 PUFA Blend. Alternatively, the Omega-6:3 PUFA Blend can contain a sulfur containing antioxidant particularly when iron is present in the food, beverage, nutritional supplement, or pharmaceutical products; one such sulfur-containing antioxidant usefully employed herein is isolated from broccoli. Yet another alternative antioxidant usefully employed with the present invention contains at least one of sulforaphane and a sulforaphane precursor glucosinolate, such as sulforaphane glucosinolate. Another embodiment of antioxidant used in the context of the present invention is ferulic acid, particularly from coffee fruit.

It is well known in the art, that the vast majority of antioxidants when utilized at high levels become pro-oxidant. The invention disclosed here establishes a unique blend of antioxidant and low omega-6 and omega-3 short-chain oil that avoids the pro-oxidant condition as compared to individual usage levels, particularly of vitamin E (i.e., mixed tocopherols). One such inventive embodiment is the inclusion of inositol on a weight basis of a range of about 25 ppm to about 100 ppm with vitamin E included in a range of about 50 ppm to about 200 ppm; in another embodiment, the inositol is included in the oil blend at about 50 ppm and the vitamin E is included in the oil blend at about 100 ppm.

In one embodiment, the blend of antioxidant is a curcumin C3 complex on a weight basis of from about 5 ppm to about 20 ppm. Inositol on a weight basis of from about 25 ppm to about 100 ppm, and vitamin E of from about 50 ppm to about 200 ppm. For example, in an example of this embodiment, the blend of antioxidant comprises at least about 10 ppm, inositol on a weight basis of at least about 50 ppm, and vitamin E of at least about 100 ppm.

Naturally occurring antioxidants can also be readily incorporated into the present invention. In addition to vitamin E compositions, which typically are a blend of tocopherols, but predominantly alpha-tocopherol, one can readily employ the herb Rosemary, for example.

One can also employ synthetic antioxidants, such as, for example, butylated hydroxyanisole "BHA"), butylated hydroxytoluene ("BHT"), and tort-butylhydroquinone ("TBHQ").

Another embodiment includes an antioxidant blend of a manganese oxide emitting a blue color at ambient temperatures on a weight basis of at least about 10 ppm, inositol on a weight basis of at least about 50 ppm and vitamin E of at least about 100 ppm.

Another approach to stabilizing the oil blends used in the context of the present invention includes use of oxygen scavengers to reduce the amount of oxygen present for oxidation of the oil. For example, one could include ascorbic acid for this purpose.

One can also extend the time of stabilized product by microencapsulation of the omega-3 fatty acids using starch or protein; or, alternatively, using medium chain triglycerides as the encapsulating agent, using methods well-known in the art.

It is also possible, and absolutely outside the scope of the present invention, to extend the shelf life of product by reducing the levels of included omega-3 fatty acids present to miniscule levels or to add flavors or aromas to mask rancidity.

For example, a product having about 32 mg per serving of omega-3 fatty acids, or less, can have a shelf life no different than that of the same product that does not include the omega-3 fatty acids. Indeed, such a low level of the omega-3 fatty acids can remain suitable for consumption in a food that has a very long shelf-life, literally years.

However, any food product that includes at least a 10% greater amount of omega-3 long-chain fatty acids relative to the aforementioned product having about 32 mg thereof per serving that is not manufactured with the ratios of fatty acids in accordance with this disclosure will readily oxidize. In consequence, such foods not having benefit of the present invention will have a shelf-life that will cut short its shelf life relative to the same food product without the higher concentration of long-chain omega-3 fatty acids. In particular, the present invention is designed for food products having, per standard serving portion, significantly higher than just a 10% increase over known prior art omega-3 enhanced foods, such as foods having at least about 50 mg of omega-3 long-chain fatty acids, or at least about 60 mg of omega-3 long-chain fatty acids, or at least about 70 mg of omega-3 long-chain fatty acids, or at least about 80 mg of omega-3 long-chain fatty acids, or at least about 90 mg of omega-3 long-chain fatty acids, or at least about 100 mg of omega-3 long-chain fatty acids, or at least about 110 mg of omega-3 long-chain fatty acids, or at least about 120 mg of omega-3 long-chain fatty acids, or at least about 130 mg of omega-3 long-chain fatty acids.

In contrast, a product manufactured in accordance with the present invention having at least 50 mg, or at least 75 mg, or at least 85 mg, or at least 95 mg, on up to at least 125 mg of omega-3 long-chain fatty acids per standard serving size will have a shelf life from no less than that of the same product made without the heightened amount of omega-3 long-chain fatty acids. Generally, the omega-3 long-chain fatty acid component of any food product that is manufactured in accordance with the present invention will itself have a shelf-life that exceeds about six months to about eight months, or 10 months, or 12 months, or 14 months, or 16 months, or 18 months, or more.

Variations in shelf life maximum exist on a per product basis. For example, the standard shelf life of dressings in the food industry is about 6 to 8 months, the standard shelf life for mayonnaise is about 5 to 7 months, the standard shelf life for breads is about 2 weeks, processed cheese is about 8 months, peanut butter is about 8 to 12 months, margarine and spreads is about 8 months refrigerated, mac and cheese dry dinner is about 12 months, and so on. One of ordinary skill in the art necessarily knows or has knowledge of how to find standard product shelf lives. The key point here is that addition of more healthful amounts of long-chain omega-3 PUFAs will not lessen the standard product shelf lives of today's food products if manufactured in accordance with the present invention.

Emulsions

The Omega-6:3 PUFA Blend is commonly used in the context of an emulsion, wherein the oil blend is prepared into an emulsion, such as a microemulsion or a nano-emulsion; accordingly, the antioxidant is subsequently added to the water phase with the already prepared Omega-6:3 PUFA Blend micro- or nano-emulsion. One method usefully employed for preparing the emulsion is the addition of medium-chain triglyceride at a weight ratio to omega-3 long-chain PUFA of at least about 0.01:1 to about 4:1, and an emulsifier at a ratio to omega-3 long-chain PUFA of at least 0.01:1 to about 5:1. In another embodiment, the ratio is between about 0.01:1 and about 1:1; in a third embodiment, the ratio is between about 0.5:1 and about 1:1; in a fourth embodiment, the ratio is between about 1:1 and about 4:1; in a fifth embodiment, the ratio is between about 1:1 and about 3:1; in a sixth embodiment, the ratio is between about 2:1 and about 3:1; in a seventh embodiment, the ratio is between about 2:1 and about 4:1; in an eighth embodiment, the ratio is between about 3:1 and about 4:1. The prepared micro- or nano-emulsion is then added to a food, thus forming a functional food, or a beverage, or a nutraceutical, or a pharmaceutical at a level of at least about 50 mg of omega-3 long-chain PUFAs per serving. Alternative embodiments of such products will include the micro- or nano-emulsion added such that the resultant functional food or nutraceutical or pharmaceutical includes per serving or pill at least about 60 mg, or at least about 70 mg, or at least about 80 mg, or at least about 90 mg, or at least about 100 mg, or at least about 110 mg, or at least about 120 mg, or at least about 130 mg.

The addition of inositol at a level of at least about 50 ppm to about 400 ppm into the oil phase prior to creating the micro- or nano-emulsion provides another tool for limiting a pro-oxidant condition when utilizing vitamin E at levels greater than about 100 ppm, and particularly at levels greater than about 300 ppm. In particular, when including tocotrienols in addition or instead of the mixed tocopherols that the formulation labeled vitamin E commonly is, it is highly desirable to include the inositol at the recited proportions with respect to vitamin E.

Triglyceride-Recrystallized Phytosterols

It is known in the art that a high level of phytosterols provides oxidative stability benefits to omega-3, but excessive levels detract from the efficacy of omega-3. In one embodiment, phytosterols are employed at relatively low levels, such as, for example, where the phytosterols component constitutes no more than about 24% by weight. It is also known that phytosterols converted from non-esterified phytosterols to triglyceride-recrystallized phytosterols provide superior performance; the present invention includes, in one embodiment, the use of recrystallized phytosterols that are converted from non-esterified phytosterols to triglyceride-recrystallized phytosterols using medium chain triglycerides. The triglyceride-recrystallized phytosterols is infused into the Omega-6:3 PUFA Blend by the following: Adding the triglyceride-recrystallized phytosterols to at least 10% by weight of carbon dioxide; Increasing the pressure of the combined triglyceride-recrystallized phytosterols and carbon dioxide to a pressure at least 3 psi greater than the supercritical pressure of carbon dioxide and a temperature of at least 2° F. greater than the supercritical temperature of carbon dioxide; adding the combined triglyceride-recrystallized phytosterols and carbon dioxide supercritical mixture to the omega-3 long-chain PUFA under rapid expansion conditions to concurrently recrystallize the phytosterols to crystal size of less than about 1000 nm to about 20 nm and decreasing the temperature of the triglyceride-recrystallized phytosterols to less than 40° C. within 60 seconds.

Preparation of Specific Food Products

In some embodiments, the oils of an Omega-6:3 PUFA Blend of the present application are utilized with a base composition suitable for the preparation of a particular food product, such as, for example and without limitation, mayonnaise, salad dressings, lite or low-calorie dressings, pasta sauces, peanut butter, sweet and salty snacks, breads, cookies and other baked items, pizzas, sauce and condiments, candies, breaded meat items, cheese, olive and olive oil blends, yogurt, drink and beverage, and the like. Food products such as these may have specific requirements to be classified as the type of product, but there is wide latitude for specific alterations to achieve desirable sensory attributes (e.g., taste, smell, feel, etc.). Such sensory attributes can be achieved through the later addition of spices, alteration of oil percentage, and the like, to prepare a finished food product. As herein contemplated, the Omega-6:3 PUFA Blend is utilized, or the individual oils of said blend are utilized in subsets thereof as noted above, by adding to the appropriate base composition in the creation of various Omega-6:3 Products.

Also contemplated are variations on standard recipes or requirements, such as mayonnaise-like food products, salad dressing-like food products, French dressing-like food products, peanut butter-like food products, etc., where variation from established standards are not generally substantive as to the nature of the food product at issue. Any recipe can be modified by one of ordinary skill in the art, such as adding the requisite ratios of oils as described herein with respect to a particular Omega-6:3 PUFA Blend, or via subsets of said oils, without there being any patentable or other distinction from applicants' claims to a particular Omega-6:3 Product.

In some embodiments, the present invention is designed to deliver at least about 50 mg of long-chain omega-3 PUFAs (i.e., DHA and EPA) per standard serving (e.g., 1 tbsp mayonnaise, 2 tbsp peanut butter, 2 tbsp salad dressing, etc.). Specific formulations of Omega-6:3 PUFA Blends may be adapted to achieve the minimum dose of long-chain omega-3 PUFAs per serving in different products (e.g., blend for mayonnaise must be different from blend for salad dressing). In particular, the present invention contemplates use of the Omega-6:3 PUFA Blends in a manner consistent with this disclosure for the manufacture of functional food products that deliver about 50 mg of DHA or EPA per serving, or about 60 mg of DHA or EPA per serving, or about 70 mg of DHA or EPA per serving, or about 80 mg of DHA or EPA per serving, or about 90 mg of DHA or EPA per serving, or about 100 mg of DHA or EPA per serving, or about 110 mg of DHA or EPA per serving, or about 120 mg of DHA or EPA per serving, or about 130 mg of DHA or EPA per serving. In yet another alternative embodiment, each of the aforementioned levels of DHA or EPA delivered per serving are considered minimums.

In some embodiments, the food base composition plus oils of the intended Omega-6:3 PUFA Blend are prepared by combining various groupings of ingredients. Exemplary groupings include oil phase ingredients, dry or powder phase ingredients, water phase ingredients, acid phase ingredients, and the like.

Oil Phase

Oil phase ingredients include, obviously, any oil(s) to be included in the Omega-6:3 Product. This would be any high oleic oil, any fish oil, any vegetable oil, any Omega-6:3 PUFA Blend or subset thereof, any hydrogenated or partially hydrogenated vegetable oil, butter, and the like. Also present in the oil phase would be any alpha-tocopherols, tocopherols, tocotrienols, medium chain triglycerides, and the like. Other ingredients usefully employed to potentiate stabilization of the oil phase ingredients can also be added.

Dry or Powder Phase

Dry or powder phase ingredients include: onion powder, garlic powder, citric acid, salt, sugar, dried egg, egg yolk powder, spices, sodium benzoate, potassium sorbate, natural flavors, gums, starches, high oleic roasted peanuts, sodium hexametaphosphate, whey protein, some acid phase ingredients, parmesan cheese, cheese blend, dried onions, dried garlic, polyglycol alginate, yeast extract, diced tomatoes, tomato paste, anchovy paste, caramel color, and the like.

Acid Phase

Acid phase ingredients include: lemon juice, vinegar, lactic acid, citric acid, phosphoric acid, and the like.

Water Phase

Water phase ingredients include: water, sugar, salt, xanthan gum, EDTA, liquid egg, liquid egg yolk, sodium benzoate, potassium sorbate, natural flavors, gums, starches, buttermilk, acid phase ingredients, tomato paste, FD&C red 40, heavy cream, butter, sodium hexametaphosphate, whey protein, parmesan cheese, cheese blend, polyglycol alginate, diced tomatoes, anchovy paste, caramel color, and the like.

Example Omega-6:3 Products

The exemplary categories and the foods therein are all known in the art and merely serve illustrative purposes to show the utility of the foregoing Omega-6:3 PUFA Blends descriptions, including subsets thereof, in standard foods within the scope of the present invention. By no means are any of the following descriptions of protocols for the identified Omega-6:3 Products meant to be limiting.

Baked Items

Baked items are made of dough and include categories such as breads, biscuits, cakes, and pastries.

Puff Pastry Dough

The composition of puff pastry dough is readily known to one of ordinary skill in the art. The following list of ingredients is merely an illustrative example and is in no way meant to be limiting. An example puff pastry dough product includes pastry flour, shortening, salt, sugar, and water.

A puff pastry food product with at least 30% by weight Omega-6:3 PUFA Blend that delivers 110 mg DHA and EPA per 100 g serving, has a short-chain omega-3 to long-chain omega-3 ratio of about 2.7:1 by weight, and has an overall omega-6 to omega-3 ratio of about 5:1 by, weight. Inositol is added to the Omega-6:3 PUFA Blend at a concentration of about 125 ppm, and vitamin E is added at a concentration of about 14 ppm.

The puff pastry dough recipe may be completed by the addition of additional ingredients (new or previously included) in proportions necessary to maintain the omega-3 and omega-6 ratios and levels.

The puff pastry dough food product may be completed by m1×mg flour and dry ingredients including salt in a dough mixer for about 2 minutes. Add water and keep mixing until the dough is ready to shape into a flat ball, and allow the dough to rest for at least 10 minutes in a cold place. Mix Omega-6:3 PUFA Blend into butter or shortening, and place the butter or high oleic shortening between two pieces of plastic wrap to pound into a flat disc using a rolling pin or other heavy object. Refrigerate for 20 minutes or until firm.

Place the disc of chilled butter in the center of the shaped dough and fold the two ends over it so that it is completely encased in dough. Roll out the dough again, taking care not to let the butter break through the dough, to about ½ inch thickness. Fold into thirds. This is the first "turn". Rotate the dough 90 degrees and roll out into a rectangle again. Fold into thirds. Place the dough on a baking sheet. Wrap in plastic and refrigerate for at least 30 minutes.

Repeat this rolling, folding and turning two more times, then refrigerate until firm. Repeat two more times for a total of 6 "turns". Wrap and refrigerate. Roll the dough out as thin as ¼ inch to make pastries. Bake in a preheated oven of at least 400° F. (200° C.).

The composition of sugar cookies is readily known to one of ordinary skill in the art. The following list of ingredients is merely an illustrative example and is in no way meant to be limiting. An example sugar cookie product includes pastry flour, milk, shortening, eggs, salt, butter, sugar, vanilla, and baking powder.

A sugar cookie food product with at least 11.3% by weight Omega-6:3 PUFA Blend that delivers 110 mg DHA and EPA per 50 g serving, has a short-chain omega-3 to long-chain omega-3 ratio of about 1.3:1 by weight, and has an overall omega-6 to omega-3 ratio of about 1.8:1 by weight. Inositol is added to the Omega-6:3 PUFA Blend at a concentration of about 125 ppm, and vitamin E is added at a concentration of about 14 ppm.

The sugar cookie recipe may be completed by the addition of additional ingredients (new or previously included) in proportions necessary to maintain the omega-3 and omega-6 ratios and levels.

The sugar cookie food product may be completed by mixing butter, sugars, and other dry ingredients together in a large dough mixer with beat liquid eggs, vanilla, and the Omega-6:3 PUFA Blend. Remaining dry ingredients are added with constant mixing to form cookie dough. Chocolate chips, nuts or other dry fruit pieces are added once the cookie dough is formed. The cookie dough is extruded thorough a wire cut cookie dough extruder which creates 1, 2, or 3 oz. cookie pieces. The baking, cooling, and packaging process follows.

White Bread

The composition of white bread is readily known to one of ordinary skill in the art. The following list of ingredients is merely an illustrative example and is in no way meant to be limiting. An example white bread product includes bread flour, non-fat milk solids, shortening, baker's yeast, salt, sugar, and water.

A white bread food product with at least 3% by weight Omega-6:3 PUFA Blend that delivers 110 mg DHA and EPA per 50 g serving, has a short-chain omega-3 to long-chain omega-3 ratio of about 1:41 by weight, and has an overall omega-6 to omega-3 ratio of about 0.3:1 by weight. Inositol is added to the Omega-6:3 PUFA Blend at a concentration of about 125 ppm, and vitamin E is added at a concentration of about 14 ppm.

The white bread recipe may be completed by the addition of additional ingredients (new or previously included) in proportions necessary to maintain the omega-3 and omega-6 ratios and levels.

The white bread food product may be completed by mixing flour and dry ingredients including salt in a dough mixer for about 2-minutes. Water yeast and the Omega-6:3 PUFA Blend are added to the water-based dough and mixed until the dough is ready. Pullman pans are filled with the dough and fermented at about 90° F. for about 2 hours manually or through a fully automated process. The fermented dough pans are baked at about 350° F. for 12-20 minutes based on size and shape. The cooled bread may be packed as either a pre-sliced r unsliced loaf.

Condiments and Dressings Mayonnaise

The ingredients and process of making mayonnaise is readily known to one of skill. The following list of ingredients is merely an illustrative example and is in no way meant to be limiting. The example mayonnaise product includes soybean oil, vinegar, liquid whole egg, salt sugar, lemon juice, garlic powder, onion powder spices, and EDTA.

A mayonnaise or mayonnaise-like food product with at least 68.9% by weight Omega-6:3 PUFA Blend that delivers 107 mg DHA and EPA per 13 g serving, has a short-chain omega-3 to long-chain omega-3 ratio of about 0.6:1 by weight, and has an overall omega-6 to omega-3 ratio of about 3.6:1 by weight. Inositol is added to the Omega-6:3 PUFA Blend at a concentration of about 125 ppm, and vitamin E is added at a concentration of about 13 ppm.

The mayonnaise recipe may be completed by the addition of additional ingredients (new or previously included) in proportions necessary to maintain the omega-3 and omega-6 ratios and levels.

The mayonnaise is processed into a finished food product by adding to a mix tank the water phase ingredients of the composition followed by liquid whole egg. The Omega-6:3 PUFA Blend, or subsets of said oils, is then added to the mixing tank. All ingredients are mixed well, and then run through a colloid mill. The batch is then pumped to storage tanks prior to packaging the finished Omega-6:3 Product.

Caesar Dressing

The ingredients of Caesar dressing are readily known to one of ordinary skill in the art. The following list of ingredients is only for illustrative purposes and is in no way meant to be limiting. The example Caesar dressing product includes soybean oil, water, parmesan cheese, distilled white vinegar, sugar, anchovy paste, salt, lactic acid, dried egg yolks, garlic powder, spices, xanthan gum, buttermilk, sodium benzoate, potassium sorbate, caramel color, and EDTA.

A Caesar salad dressing or salad dressing-like food products with at least 47% by weight Omega-6:3 PUFA Blend delivers 126 mg DHA and EPA per 32 g serving, has a short-chain omega-3 to long-chain omega-3 ratio of about 2:1 by weight, and has an overall omega-6 to omega-3 ratio of about 3:1 by weight. Inositol is added to the Omega-6:3 PUFA Blend at a concentration of about 125 ppm, and vitamin E is added at a concentration of about 16 ppm.

The Caesar dressing recipe may be completed by the addition of additional ingredients (new or previously included) in proportions necessary to maintain the omega-3 and omega-6 ratios and levels.

The Caesar salad dressing is processed into a finished food product by adding to a mixing tank all water phase ingredients. The agitator in the mixing tank is turned on, and the starchy paste is added and distributed. The rest of the dry ingredients are added to the mixing tank, and the batch is mixed until the dry ingredients have dissolved. The Omega-6:3 PUFA Blend, or individual oils thereof, is then added to the mixing tank, and the batch is run through a colloid mill. The batch is then pumped into a particle tank, where spices are added, and then the finished food product is packaged.

Red French-Style Dressing

The composition of traditional red French-style dressing is readily known to one of ordinary skill in the art. The following list of ingredients is merely an illustrative example and is in no way meant to be limiting. An example red French-style dressing product includes sugar, water, soybean oil, distilled white vinegar, tomato paste, salt, modified food starch, phosphoric acid, onion powder, xanthan gum, potassium sorbate, FD&C Red 40, and EDTA. A French or French-style dressing product with at least 18% by weight Omega-6:3 PUFA Blend that delivers 101 mg DHA and EPA per 32 g serving, has a short-chain omega-3 to long-chain omega-3 ratio of about 1.5:1 by weight, and has an overall omega-6 to omega-3 ratio of about 2:1 by weight. Inositol is added to the Omega-6:3 PUFA Blend at a concentration of about 125 ppm, and vitamin E is added at a concentration of about 13 ppm.

The red French style dressing base product recipe may be completed by the addition of additional ingredients (new or previously included) in proportions necessary to maintain the omega-3 and omega-6 ratios and levels.

The French-style dressing base food product is processed into a finished food product by adding to a mixing tank all water phase ingredients. The agitator in the mixing tank is turned on, and the starchy paste is added and distributed. The rest of the dry ingredients are added to the mixing tank, and the batch is mixed until the dry ingredients have dissolved. The Omega-6:3 PUFA Blend, or its component oils separately, is then added to the mixing tank, and the batch is run through a colloid mill. The batch is then pumped into a particle tank, where spices are added, and then the finished food product is packaged.

Ranch-Style Salad Dressing

The composition of traditional ranch-style dressing is readily known to one of ordinary skill in the art. The following list of ingredients is merely an illustrative example and is in no way meant to be limiting. An example ranch-style dressing product includes buttermilk, soybean oil, vinegar, sugar cane, salt, egg yolk powder, gum, onion powder, lemon juice, lactic acid, modified food starch polyglycol alginate, sodium benzoate, and EDTA. A Ranch-style salad dressing or salad dressing-like food product with at least 59% by weight Omega-6:3 PUFA Blend, or the oils thereof, that delivers 112 mg DHA and EPA per 30 g serving, has a short-chain omega-3 to long-chain omega-3 ratio of about 4:1 by weight, and has an overall omega-6 to omega-3 ratio of about 3:1 by weight. Inositol is added to the Omega-6:3 PUFA Blend at a concentration of about 125 ppm, and vitamin E is added at a concentration of about 14 ppm.

The Ranch style dressing base product recipe may be completed by the addition of additional ingredients (new or previously included) in proportions necessary to maintain the omega-3 and omega-6 ratios and levels.

The Ranch-style salad dressing base food product is processed into a finished food product by adding to a mixing tank all water phase ingredients. The agitator in the mixing tank is turned on, and the starchy paste is added and distributed. The rest of the dry ingredients are added to the mixing tank, and the batch is mixed until the dry ingredients have dissolved. The Omega-6:3 PUFA Blend, or the oils thereof, is then added to the mixing tank, and the batch is run through a colloid 10 mill. The batch is then pumped into a particle tank, where spices are added, and then the finished food product is packaged.

Blue Cheese Dressing

The composition of blue cheese dressing is readily known to one of ordinary skill in the art. The following list of ingredients is merely an illustrative example and is in no way meant to be limiting. An example blue cheese dressing product includes soybean oil, water, blue cheese, vinegar, buttermilk, sugar, salt, egg yolk, provesta, blue cheese flavor, xanthan gum, garlic powder, onion powder, starch, propylene glycol alginate, polysorbate 60, potassium sorbate, sodium benzoate, black pepper, parsley, garlic juice, and calcium disodium EDTA.

A blue cheese dressing with at least 50% by weight Omega-6.3 PUFA Blend delivers about 105 mg DHA and EPA per 30 g serving, has a short-chain omega-3 to long-chain omega-3 ratio of about 2.5:1 by weight, and has an overall omega-6 to omega-3 ratio of about 3:1 by weight. Inositol is added to the Omega-6:3 PUFA Blend at a concentration of about 125 ppm, and vitamin E is added at a concentration of about 13 ppm.

The blue cheese dressing recipe may be completed by the addition of additional ingredients (new or previously included) in proportions necessary to maintain the omega-3 and omega-6 ratios and levels.

The blue cheese dressing is processed into a finished food product by adding to a mixing tank all water phase ingredients which include the antioxidants. The agitator in the mixing tank is turned on, and the starchy paste is added and distributed. The rest of the dry ingredients are added to the mixing tank, and the batch is mixed until the dry ingredients have dissolved. The Omega-6:3 PUFA Blend, or oils thereof, is then added to the mixing tank, and the batch is run through a colloid mill. The batch is then pumped into a particle tank, where spices are added, and then the finished food product is packaged.

The composition of Italian dressing is readily known to one of ordinary skill in the art. The following list of ingredients is merely an illustrative example and is in no way meant to be limiting. An example Italian dressing product includes canola oil, water, garlic, vinegar, minced onion, sugar, salt, minced garlic, xanthan gum, bell pepper granules, mono and diglycerides, yellow #6, potassium sorbate, oregano leaf, basil, paprika, and calcium disodium EDTA.

An Italian dressing product with at least 20% by weight Omega-6:3 PUFA Blend delivers 118 mg DHA and EPA per 30 g serving, has a short-chain omega-3 to long-chain omega-3 ratio of about 1:1 by weight, and an overall omega-6 to omega-3 ratio of about 2:1 by, weight. Inositol is added to the Omega-6:3 PUFA Blend at a concentration of about 125 ppm, and vitamin E is added at a concentration of about 15 ppm.

The Italian dressing recipe may be completed by the addition of additional ingredients (new or previously included) in proportions necessary to maintain the omega-3 and omega-6 ratios and levels.

The Italian dressing food product may be completed by mixing the dry ingredients in a Hobart mixer. Vinegar, lemon juice, and water are slowly mixed into the dry mix and added into the Omega-6:3 PUFA Blend. Salad oil is then added in a steady stream while mixing.

Horseradish Sauce

The composition of horseradish sauce is readily known to one of ordinary skill in the art. The following list of ingredients is merely an illustrative example and is in no way meant to be limiting. An example horseradish sauce product includes soybean oil, water, vinegar, salt, egg yolks, sugar, egg whites, powdered whole eggs, mustard flour, garlic powder, onion powder, EDTA oleoresin paprika, and pure horseradish roots.

A horseradish sauce food product with at least 67% by weight Omega-6:3 PUFA Blend that delivers at least 55 mg DHA and EPA per 15 g serving, has a short-chain omega-3 to long-chain omega-3 ratio of about 3.5:1 by weight, and has an overall omega-6 to omega-3 ratio of about 4.6:1 by weight. Inositol is added to the Omega-6:3 PUFA Blend at a concentration of about 125 ppm, and vitamin E is added at a concentration of about 7 ppm.

The horseradish sauce recipe may be completed by the addition of additional ingredients (new or previously included) in proportions necessary to maintain the omega-3 and omega-6 ratios and The horseradish sauce food product may be completed by grinding the roots and mixing the ground root with sweeteners and spices in a kettle. Vinegar, mustard powder and the other remaining ingredients are mixed in. Omega-6:3 PUFA Blend, or the oils thereof, is mixed into the water-based sauce to a uniform consistency. If the horseradish sauce food product is a high oil/creamy based/emulsion formulation, do not heat process. Food safety is accomplished through acid, moisture and salt balance and the product is ready to pack.

If the horseradish food product is a water-based sauce, depending on the acid, moisture and salt content level, heat processing might be necessary. Heat processing comprises heating the water-based sauce to 190° F., and hot filling or aseptically filling into final packaging containers.

Ketchup Sauce

The composition of ketchup is readily known to one of ordinary skill in the art. The following list of ingredients is merely an illustrative example and is in no way meant to be limiting. An example ketchup product includes tomato paste, water, distilled vinegar, high fructose corn syrup, instant starch, salt, onion powder, allspice, cloves, cinnamon, garlic powder, celery powder, and lecithin.

A ketchup sauce food product with at least 3% by weight Omega-6:3 PUFA Blend that delivers at least 55 mg DHA and EPA per 17 g serving, has a short-chain omega-3 to long-chain omega-3 ratio of about 1:46 by weight, and has an overall omega-6 to omega-3 ratio of about 0.001:60 by weight. Inositol is added to the Omega-6:3 PUFA Blend at a concentration of about 125 ppm. Vitamin E is included with the oil phase resulting in an overall concentration of about 0.02 ppm. Inositol is added during processing of the ketchup sauce food product with the water phase ingredients resulting in an overall concentration of about 125 ppm, and vitamin E is added at a concentration of about 7 ppm.

The ketchup recipe may be completed by the addition of additional ingredients (new or previously included) in proportions necessary to maintain the omega-3 and omega-6 ratios and levels.

The ketchup sauce food product may be completed by mixing tomato or any other type of paste and water together into a mixer/blender or high shear equipment or a cooking kettle to achieve a uniform texture mixture. Dry ingredients, flavors, colors and oils and mixed in with the tomato slurry until the sugar is completely dissolved. The Omega-6:3 PUFA Blend, or the oils thereof, is added to this water phase sauce in a kettle and heated to about 165° F., Hot fill or aseptically fill into final packaging containers.

Mustard Sauce

The composition of mustard is readily known to one of ordinary skill in the art. The following list of ingredients is merely an illustrative example and is in no way meant to be limiting. An example mustard sauce product includes water, distilled vinegar, mustard seed flour, salt, turmeric powder, paprika, and garlic powder.

A mustard sauce food product with at least 3% by weight Omega-6:3 PUFA Blend that delivers at least 55 mg DHA and EPA per 15 g serving, has a short-chain omega-3 to long-chain omega-3 ratio of about 1:61 by weight, and has an overall omega-6 to omega-3 ratio of about 0.001:60 by weight. Inositol is added to the Omega-6:3 PUFA Blend at a concentration of about 125 ppm, and vitamin is added at a concentration of about 7 ppm.

The mustard sauce recipe may be completed by the addition of additional ingredients (new or previously included) in proportions necessary to maintain the omega-3 and omega-6 ratios and levels.

The mustard sauce food product may be completed by grinding mustard seeds soaked for at least two hours before grinding. Sweeteners and spices are mixed into the ground seeds in a commercial cooking kettle with a speed adjustable mixer. Vinegar, other remaining ingredients, and Omega-6:3 PUFA Blend, or the oils thereof, is mixed into the water-based sauce until a uniform consistency is achieved. The batch is mixed and heated to 190° F. Hot fill or aseptically fill into final packaging containers.

Grocery Items

Grocery items are foods sold in a grocery store.

Pasta Sauce

The composition of red pasta sauce, traditional, marinara, sun dried tomato and basil pesto is readily known to one of ordinary skill in the art. The following list of ingredients is merely an illustrative example and is in no way meant to be limiting. The example traditional red pasta sauce product includes water, tomato paste, diced tomatoes, soybean oil, salt, sugar, garlic, onion powder, oregano, basil, ground fennel seeds, citric acid, and black pepper.

A pasta sauce food product with at least 2% by weight Omega-6:3 PUFA Blend delivers at least 103 mg DHA and EPA per 126 g serving, has a short-chain omega-3 to long-chain omega-3 ratio of about 3:10 by weight, and an overall omega-6 to omega-3 ratio of about 1.5:1 by weight. Inositol is added to the Omega-6:3 PUFA Blend at a concentration of about 125 ppm, and vitamin E is added at a concentration of about 13 ppm.

The pasta sauce base product recipe may be completed by the addition of additional ingredients (new or previously included) in proportions necessary to maintain the omega-3 and omega-6 ratios and levels.

The pasta sauce base food product is processed into a finished food product by adding water phase ingredients to a batch tank. The contents of the batch tank are mixed until uniform. Once uniform, the Omega-6:3 PUFA Blend is added to the hatch, which is then run through the tube in a tube heat processor and into the filler hold tank prior to packaging the finished food product.

Alfredo Sauce

The composition of alfredo sauce is readily known to one of ordinary skill in the art. The following list of ingredients is merely an illustrative example and is in no way meant to be limiting. The example alfredo sauce product includes water, heavy cream, parmesan cheese, modified food starch, butter, soybean oil, cheese blend, sugar, sodium hexametaphosphate, salt, dried egg, whey protein, garlic powder, lactic acid, onion powder, and ground white pepper. An alfredo sauce with at least 1% by weight Omega-6:3 PUFA Blend that delivers 168 mg DHA and EPA per 126 g serving, has a short-chain omega-3 to long-chain omega-3 ratio of about 0.7:1 by weight, and has an overall omega-6 to omega-3 ratio of about 2:1 by weight. Inositol is added to the Omega-6:3 PUFA Blend at a concentration of about 125 ppm, and vitamin E is added at a concentration of about 21 ppm.

The alfredo sauce base product recipe may be completed by the addition of additional ingredients (new or previously included) in proportions necessary to maintain the omega-3 and omega-6 ratios and levels.

The alfredo sauce base food product is processed into a finished food product by adding to a mixing tank all water phase ingredients. The agitator in the mixing tank is turned on, and the starchy paste is added and distributed. The rest of the dry ingredients are added to the mixing tank, and the batch is mixed until the dry ingredients have dissolved. The Omega-6:3 PUFA Blend, or oils thereof, is then added to the mixing tank, and the batch is run through a colloid mill. The batch is then pumped into a particle tank, where spices are added, and then the finished food product is packaged.

Peanut Butter

The composition of peanut butter is readily known to one of ordinary skill in the art. The following list of ingredients is merely an illustrative example and is in no way meant to be limiting. An example peanut butter product includes roasted peanuts, sugar, salba seed, modified palm oil, salt, and EDTA. A peanut butter or peanut butter-like food product with at least 1% by weight Omega-6:3 PUFA Blend, or oils thereof, delivers at least 105 mg DHA and EPA per 32 g serving, has a short-chain omega-3 to long-chain omega-3 ratio of about 2.5:1 by weight, and an overall omega-6 to omega-3 ratio of about 3:1 by weight. Inositol is added to the Omega-6:3 PUFA Blend at a concentration of about 125 ppm, and vitamin E is added at a concentration of about 13 ppm.

The peanut butter base product recipe may be completed by the addition of additional ingredients (new or previously included) in proportions necessary to maintain the omega-3 and omega-6 ratios and levels.

The base food product is processed into a finished food product by grinding the roasted and blanched peanuts with the other ingredients. Before a second grinding the Omega-6:3 PUFA blend is added to the ground product. The peanut butter food product is de-aerated after the second grinding and packaged.

Macaroni and Cheese

The composition of macaroni and cheese is readily known to one of ordinary skill in the art. The following list of ingredients is merely an illustrative example and is not way meant to be limiting. An example macaroni and cheese product includes macaroni pasta, shortening powder, dried sweet whey, triglyceride, salt, natural cheese flavoring, monosodium glutamate, yellow #5, Yellow #6, whey, salt, granular cheese, cheddar, butter, sodium tripolyphosphate, citric acid, disodium phosphate, butter flavoring, and water.

A macaroni and cheese food product with at least 7% by weight Omega-6:3 PUFA Blend, or oils thereof, that delivers at least 121 mg DHA and EPA per 220 g serving, has a short-chain omega-3 to long-chain omega-3 ratio of about 0.3:1 by weight, and has an overall omega-6 to omega-3 ratio of about 0.5:1 by weight. Inositol is added to the Omega-6:3 PUFA Blend at a concentration of about 125 ppm, and vitamin E is added at a concentration of about 15 ppm.

The macaroni and cheese recipe may be completed by the addition of additional ingredients (new or previously included) in proportions necessary to maintain the omega-3 and omega-6 ratios and levels.

The macaroni and cheese food product may be completed by grinding natural cheese pieces and heating the grinded cheese in a horizontal scrape surface cheese cooker with a salt slurry and a whey slurry to 170° F. The Omega-6:3 PUFA Blend is added to this cheese emulsion and mixed another 60 seconds. The process cheese slurry is either liquid packed or transferred to a milk dryer and turned into cheese powder through a pulverization process and portion packed into 1.5 oz pouches. Portion packed powder or liquid cheese pouches are further packed with pasta into meals boxes. Different size and shape pasta pieces can be used, such as spirals, tubes, whole wheat, organic, etc.

Corn Snacks

The composition of corn snacks are readily known to one of ordinary skill in the art. The following list of ingredients is merely an illustrative example and is in no way meant to be limiting. An example corn snack product includes corn flour, water, flour salt, and palm kernel oil shortening.

A corn snack food product with at least 1.7% by weight Omega-6:3 PUFA Blend, or oils thereof, that delivers at least 106 mg DHA and EPA per 57 g serving, has a short-chain omega-3 to long-chain omega-3 ratio of about 0.03:1 by weight, and has an overall omega-6 to omega-3 ratio of at least 1:9 by weight. Inositol is added to the Omega-6:3 PIMA Blend at a concentration of about 125 ppm, and vitamin E is added at a concentration of about 13 ppm.

The corn snack recipe may be completed by the addition of additional ingredients (new or previously included) in proportions necessary to maintain the omega-3 and omega-6 ratios and levels. The corn snack food product may be completed by mixing the corn flour oil flakes with salt and water. The mixture is passed through a sing screw extruder with an internal temperature set at about 275° F. to 300° F. The snack curls are cooled and sprayed with the Omega-6:3 PUFA Blend in a tumbler. Cheese or other flavors may optionally be mixed in with the snack curls in the tumbler.

Potato Chips

The composition of potato chips is readily known to one of ordinary skill in the art. The following list of ingredients is merely an illustrative example and is in no way meant to be limiting. An example potato chip product includes potatoes, canola frying oil, and salt.

A potato chip food product with at least 35% by weight Omega-6:3 PUFA Blend, or oils thereof, that delivers at least 79 mg DHA and EPA per 28 g serving, has a short-chain omega-3 to long-chain omega-3 ratio of about 5:1 by weight, and has an overall omega-6 to omega-3 ratio of about 4:1 by weight. Inositol is added to the Omega-6:3 PUFA Blend, or oils thereof, at a concentration of about 125 ppm, and vitamin E is added at a concentration of about 3 ppm.

The potato chip recipe may be completed by the addition of additional ingredients (new or previously included) in proportions necessary to maintain the omega-3 and omega-6 ratios and levels.

The potato chip food product may be completed by frying cleaned, peeled and sliced potatoes in the Omega-6:3 PUFA Blend, or the oils thereof, at 350° F. for a minimum of about 2 minutes. During this frying time, moisture exchanged with balanced oil (oil pick up from the fryer) is enriched with omega-3. Later enriched fried potatoes chips are gently salted, seasoned and packed into nitrogen flashed pillow bags.

Strawberry Jam

The composition of strawberry jam is readily known to one of ordinary skill in the art. The following list of ingredients is merely an illustrative example and is in no way meant to be limiting. An example strawberry jam product includes sugar, strawberry jam base, citrus pectin, water, and citric acid.

A strawberry jam food product with at least 4% by, weight Omega-6:3 PUFA Blend, or oils thereof, delivers at least 101 mg DHA and EPA per 20 g serving, has a short-chain omega-3 to long-chain omega-3 ratio of about 1:61 by weight, and has an overall omega-6 to omega-3 ratio of about 0.001:119 by weight. Inositol is added to the Omega-6:3 PUFA Blend at a concentration of about 125 ppm, and vitamin E is added at a concentration of about 13 ppm.

The strawberry jam recipe may be completed by the addition of additional ingredients (new or previously included) in proportions necessary to maintain the omega-3 and omega-6 ratios and levels.

The strawberry jam food product may be completed by mixing pectin and texture aid dry powder ingredients such as sugar and citric and other ingredients in a cooking kettle. Water is mixed into the cooking kettle with concurrent heating to create uniform slurry texture. Fruit pieces and Omega-6:3 PUFA Blend, or the oils thereof, are added to this water base slurry and cooked to 210° F. The slurry is then hot fill packaged. As known to one of ordinary skill in the art, depending on the pectin type used either a single stage or double stage cooling process is applied.

Apple Sauce

The composition of apple sauce is readily known to one of ordinary skill in the art. The following list of ingredients is merely an illustrative example and is in no way meant to be limiting. An example apple sauce product includes apples, sugar, water, and ascorbic acid.

An apple sauce food product with at least 0.3% by weight Omega-6:3 PUFA Blend, or oils thereof, that delivers at least 110 mg DHA and EPA per 340 g serving, has a short-chain omega-3 to long-chain omega-3 ratio of about 1:61 by weight, and has an overall omega-6 to omega-3 ratio of about 0.001:119 by weight. Inositol is added to the Omega-6:3 PUFA Blend at a concentration of about 125 ppm, and vitamin E is added at a concentration of about 14 ppm.

The apple sauce recipe may be completed by the addition of additional ingredients (new or previously included) in proportions necessary to maintain the omega-3 and omega-6 ratios and levels.

The apple sauce food product may be completed by blending peeled and diced apples with sugar and seasonings. The Omega-6:3 PUFA Blend, or oils thereof, is added to the water base slurry in a steam kettle and eat processed for a hot filling, packaging and cooling process.

Desserts

Desserts are the sweet course, typically eaten at the end of a meal.

Frozen Fruit Desserts

The composition of frozen fruit desserts are readily known to one of ordinary skill in the art. The following list of ingredients is merely an illustrative example and is in no way meant to be limiting. As an example, a frozen strawberry dessert product includes strawberry puree, citric acid, sucrose, strawberry flavoring, xanthan gum, and water.

A frozen fruit dessert food product with at least 0.3% by weight Omega-6:3 PUFA Blend, or oils thereof, that delivers at least 110 mg DHA and EPA per 340 g serving, has a short-chain omega-3 to long-chain omega-3 ratio of about 1:61 by weight, and has an overall omega-6 to omega-3 ratio of about 0.001:119 by weight. Inositol is added to the Omega-6:3 PUFA Blend at a concentration of about 125 ppm, and vitamin E is added at a concentration of about 14 ppm.

The frozen fruit dessert recipe may be completed by the addition of additional ingredients (new or previously included) in proportions necessary to maintain the omega-3 and omega-6 ratios and levels.

The frozen fruit dessert food product may be completed by first mixing Omega-6:3 PUFA Blend, or oils thereof, fruit puree, sugar and water in a high sheer blender to create a uniform mix. The beverage slurry is then cooked to 190° F. The heat processed dessert mix is then put through a preliminary freezing process where the slurry temperature is decreased to 10° F. slushy/semisolid form. This semi-solid product is packed into cups or turned into bars. The packed desserts go through a second freezing or hard freezing process which is below −20° F.

The composition of ice cream is readily known to one of ordinary skill in the art. The following list of ingredients is merely an illustrative example and is in no way meant to be limiting. An example ice cream product includes milk fat, non-fat milk solids, sucrose, corn syrup, a stabilizing gum and pectin, an emulsifying gum and pectin, and vanilla flavoring.

An ice cream food product with at least 25% by weight Omega-6:3 PUFA Blend, or oils thereof, that delivers at least 50 mg DHA and EPA per 70 g serving, has a short-chain omega-3 to long-chain omega-3 ratio of about 0.5:1 by weight, and has an overall omega-6 to omega-3 ratio of about 0.5:1 by weight. Inositol is added to the Omega-6:3 PUFA Blend, or the oils thereof, at a concentration of about 125 ppm, and vitamin E is added at a concentration of about 6 ppm.

The ice cream recipe may be completed by the addition of additional ingredients (new or previously included) in proportions necessary to maintain the omega-3 and omega-6 ratios and levels.

The ice cream food product may be completed by mixing the Omega-6:3 PUFA Blend, or the oils thereof, ice cream mix, sugar and water in a high sheer blender to create a uniform mix. The slurry is then cooked to 190° F. The heat processed mix is then put through a preliminary freezing process where the slurry temperature is decreased to 10° F. slushy/semisolid form. This semi-solid product is packed into cups or turned into bars. The packed ice cream goes through a second freezing or hard freezing process which is below −20° F.

Frozen Yogurt

The composition of frozen yogurt is readily known to one of ordinary skill in the art. The following list of ingredients is merely an illustrative example and is in no way meant to be limiting. An example frozen yogurt product includes milk fat, non-fat milk solids, sucrose, corn syrup, stabilizing gums and pectins, emulsifying gums and pectins, and vanilla. Typically, bacteria such as *Lactobacillus delbrueckii* or *Streptococcus thermophilus* are added to a portion of milk that has been previously heated to about 90° C. for about 15 min. The mixture is then incubated at a temperature range from about 35° C. to 45° C. to bring the pH to lower than about 5.

Frozen yogurt within the scope of the current invention includes Omega-6:3 PUFA Blend, or the oils thereof.

A frozen yogurt food product with at least 10% by weight Omega-6:3 PUFA Blend that delivers at least 107 mg DHA and EPA per 90 g serving, has a short-chain omega-3 to long-chain omega-3 ratio of about 0.3:1 by weight, and has an overall omega-6 to omega-3 ratio of about 0.3:1 by weight. Inositol is added to the Omega-6:3 PUFA Blend at a concentration of about 125 ppm, and vitamin E is added at a concentration of about 4 ppm.

The frozen yogurt recipe may be completed by the addition of additional ingredients (new or previously included) in proportions necessary to maintain the omega-3 and omega-6 ratios and levels.

The frozen yogurt product may be completed by mixing the Omega-6:3 PUFA Blend, or oils thereof, frozen yogurt mix, sugar and water in a high sheer blender to create a uniform mix. The slurry is then cooked to 190° F. The heat processed mix is then put through a preliminary freezing process where the slurry temperature is decreased to 10° F. slushy/semisolid form. This semi-solid product is packed into cups or turned into bars. The packed ice cream goes through a second freezing or hard freezing process which is below −20° F.

Chocolate Pudding

The composition of chocolate pudding is readily known to one of ordinary skill in the art. The following list of ingredients is merely an illustrative example and is in no way meant to be limiting. An example chocolate pudding product includes chocolate, starch, sugar, tetrasodium pyrophosphate, disodium phosphate, salt, artificial and natural vanilla flavoring, xanthan gum, condensed milk, partially hydrogenated soybean oil, caramel coloring, calcium sulfate dehydrate, acesulfame potassium, and butylated hydroxyanisole ("BHA").

A chocolate pudding food product with at least 20% by weight Omega-6:3 PUFA Blend, or oils thereof, delivers at least 100 mg DHA and EPA per 100 g serving, has a short-chain omega-3 to long-chain omega-3 ratio of about 0.02:1 by weight, and has an overall omega-6 to omega-3 ratio of about 0.001:109 by weight. Inositol is added to the Omega-6:3 PUFA Blend, or oils thereof, at a concentration of about 125 ppm, and vitamin E is added at a concentration of about 12 ppm.

The chocolate pudding recipe may be completed by the addition of additional ingredients (new or previously included) in proportions necessary to maintain the omega-3 and omega-6 ratios and levels.

The chocolate pudding food product may be completed by mixing all dry ingredients with cold water in a cooking kettle. Oil, butter, and Omega-6:3 blend is added to the water-based slurry. The slurry is heated to a boil while mixing. The food product is packaged by in-line aseptic cooling and packaging (form fill and seal) or cold aseptic fill seal and cupping and pouching.

Vanilla Pudding

The composition of vanilla pudding is readily known to one of ordinary skill in the art. The following list of ingredients is merely an illustrative example and is in no way meant to be limiting. An example Boston cream style vanilla pudding product includes white chocolate, starch, sugar, tetrasodium pyrophosphate, disodium phosphate, salt, artificial and natural vanilla flavoring, xanthan gum, tetrapotassium pyrophosphate, condensed milk artificial flavoring, dipotassium phosphate, partially hydrogenated soybean oil, calcium sulfate dehydrate, acesulfame potassium, butylated hydroxyanisole ("BHA"), and annatto.

A vanilla pudding food product with at least 1% by weight Omega-6:3 PUFA Blend that delivers at least 101 mg DHA and EPA per 100 g serving, has a short-chain omega-3 to long-chain omega-3 ratio of about 1:61 by weight, and has an overall omega-6 to omega-3 ratio of about 0.001:119 by weight. Inositol is added to the Omega-6:3 PUFA Blend, or oils thereof, at a concentration of about 125 ppm, and vitamin E is added at a concentration of about 13 ppm.

The vanilla pudding recipe may be completed by the addition of additional ingredients (new or previously included) in proportions necessary to maintain the omega-3 and omega-6 ratios and levels.

The vanilla pudding food product may be completed by mixing all dry ingredients with cold water in a cooking kettle. While heating the mixture to a boil, oil or butter and Omega-6:3 PUFA Blend are added to the water-based slurry. Packaging may be performed by inline aseptic cooling and packaging (form fill and seal) or cold aseptic fill seal and cupping and pouching.

Deli or Delicatessen

Deli or delicatessen is a term meant for specially prepared foods.

Processed Cheese Sauce

The composition of processed cheese sauce is readily known to one of ordinary skill in the art. The following list of ingredients is merely an illustrative example and is in no way meant to be limiting. An example processed cheese sauce product includes natural cheese blend, water, butter, salt, skim milk powder, dried sweet whey, dried whey protein concentrate, maltodextrin, sorbates, and annatto.

A processed cheese sauce food product with at least 3% by weight Omega-6:3 PUFA Blend, or oils thereof, delivers at least 110 mg DHA and EPA per 32 g serving, has a short-chain omega-3 to tong-chain omega-3 ratio of about 0.3:1 by weight, and has an overall omega-6 to omega-3 ratio of about 2:1 by weight. Inositol is added to the Omega-6:3 PUFA Blend, or oils thereof, at a concentration of about 125 ppm, and vitamin E is added at a concentration of about 14 ppm.

The processed cheese sauce recipe may be completed by the addition of additional ingredients (new or previously included) in proportions necessary to maintain the omega-3 and omega-6 ratios and levels.

The processed cheese food product may be completed by mixing, a salt slurry, a whey slurry and cheese mix in a horizontal cheese cooker. Then heating the slurry through a scrape surface heat exchanger to 170° F. The Omega-6:3 PUFA Blend is added to this cheese emulsion and mixed another 30 seconds. The processed cheese sauce food product is then packed and cooled.

Margarine Spreads

The composition of margarine is readily known to one of ordinary skill in the art. The following list, of ingredients is merely an illustrative example and is not way meant to be limiting. An example margarine spread product includes canola oil, lecithin, mono- and diglycerides, salt, beta-carotene, benzoic acid, calcium triphosphate, butylated hydroxytoluene (BHT), EDTA, and water.

A margarine spread food product with at least 80% by weight Omega-6:3 PUFA Blend, or oils thereof, delivers at least 308 mg DHA and EPA per 14 g serving, has a short-chain omega-3 to long-chain omega-3 ratio of at least 2:1 by weight, and has an overall omega-6 to omega-3 ratio of about 3.6:1 by weight. Inositol is added to the Omega-6:3 PUFA Blend at a concentration of about 125 ppm, and vitamin E is added at a concentration of about 38 ppm.

The margarine spread recipe may be completed by the addition of additional ingredients (new or previously included) in proportions necessary to maintain the omega-3 and omega-6 ratios and levels.

The margarine spread food product may be completed by mixing or blending refined oils together to make the right texture for the final spread product. The refined oil is blended with vitamins, Omega-6:3 PUFA Blend, or oils thereof, colors, flavors and emulsifiers. At the same time a mixture of water, whey, brine and powdered ingredients is created in another tank. These two ingredient mixtures are blended together at temperatures of about 50-60° C. while being slightly mixed. This water-in-oil ("W/O") emulsion is pasteurized at temperatures about 70 to 86° C. The mixed spread is chilled to a solid. During the chilling process, the product is transferred to a cylindrical chamber to knead the spread at a fixed speed. Margarine is transported to a packing line.

Cream Cheese

The composition of cream cheese is readily known to one of ordinary skill in the art. The following list of ingredients is merely an illustrative example and is in no way meant to be limiting. An example cream cheese product includes pasteurized non-fat milk, pasteurized milk cream, carob bean gum, salt, xanthan gum, and *Lactococcus lactis*.

A cream cheese food product with at least 34% by weight Omega-6:3 PUFA Blend, or oils thereof, delivers at least 264 mg DHA and EPA per 220 g serving, has a short-chain omega-3 to long-chain omega-3 ratio of about 11.2:1 by weight, and has an overall omega-6 to omega-3 ratio of at least 4:1 by weight. Inositol is added to the Omega-6:3 PUFA Blend, or oils thereof, at a concentration of about 125 ppm, and vitamin E is added at a concentration of about 33 ppm. The cream cheese recipe may be completed by the addition of additional ingredients (new or previously included) in proportions necessary to maintain the omega-3 and omega-6 ratios and levels.

The cream cheese food product may be completed by adding texture aid gums and or pectin to full fat milk. The milk is pasteurized and standardized with a maximum of 3.5 percent fat. The milk is homogenized at a temperature of about 50-70° C. Bacterial culture are added at about 22° C. and fermented to a desired pH and flavor. The Omega-6:3 PUFA Blend, or oils thereof, is then added to this water-based milk. The whey is drained and the curd is heat treated at 70° C. for 3 to 30 minutes. The curd is packaged into molds or containers after degassing and chilled to 2° C.

Hummus Spread

The composition of hummus spread is readily known to one of ordinary skill in the art. The following list of ingredients is merely an illustrative example and is in no way meant to be limiting. An example hummus spread product includes cooked garbanzo beans, tahini paste, canola oil, salt, garlic, cumin powder, lemon juice, potassium sorbate, sodium benzoate, black pepper, and garlic aqua resin.

An hummus spread food product with at least 4.9% by weight Omega-6:3 PUFA Blend, or oils thereof, delivers 358 mg DHA and EPA per 113 g serving, has a short-chain omega-3 to long-chain omega-3 ratio of about 1:10 by weight, and has an overall omega-6 to omega-3 ratio of about 0.7:1 by weight. Inositol is added to the Omega-6:3 PUFA Blend, or oils thereof, at a concentration of about 125 ppm, and vitamin E is added at a concentration of about 45 ppm.

The hummus spread recipe may be completed by the addition of additional ingredients (new or previously included) in proportions necessary to maintain the omega-3 and omega-6 ratios and levels.

The hummus spread food product may be completed by cooking presoaked beans to a desired texture, adding spices oils, salt and seasoning and preservatives and grinding the mixture to a paste-like product. Before grinding/size reduction add. Omega-6:3 PUFA Blend into the soaked bean mixture. Further process the paste into a desired puree texture, pack, and store.

Refried Bean Dip

The composition of refried bean dip is readily known to one of ordinary skill in the art. The following list of ingredients is merely an illustrative example and is not way meant to be limiting. An example refried bean dip product includes cooked pinto beans, water, canola oil, salt, chili powder, onion powder, cumin powder, and ground black pepper.

A refried bean dip food product with at least 3% by weight Omega-6:3 PUFA Blend delivers 250 mg DHA and EPA per 236 g serving, has a short-chain omega-3 to long-chain omega-3 ratio of about 1:3 by weight, and has an overall omega-6 to omega-3 ratio of about 1.7:1 by weight. Inositol is added to the Omega-6:3 PUFA Blend, or oils thereof, at a concentration of about 125 ppm, and vitamin E is added at a concentration of about 31 ppm.

The refried bean dip recipe may be completed by the addition of additional ingredients (new or previously included) in proportions necessary to maintain the omega-3 and omega-6 ratios and levels.

The refried bean dip food product may be completed by cooking presoaked beans to a desired texture, adding spices oils, salt and seasoning and preservatives and grinding the mixture to a paste-like product. Before grinding/size reduction add Omega-6:3 PUFA Blend, or oils thereof, into the soaked bean mixture. Further process the paste into a desired puree texture, pack, and store.

Chicken Nuggets

The composition of chicken nuggets is readily known to one of ordinary skill in the art. The following list of ingredients is merely an illustrative example and is in no way meant to be limiting. An example chicken nugget food product includes pre-sliced chicken white meat breast, breadcrumbs, salt, soluble black pepper, garlic powder, Dakota flour, whole dried egg, soy sauce, and teriyaki sauce.

A chicken nugget food product with at least 0.4% by weight Omega-6:3 PUFA Blend, or oils thereof, that delivers at least 102 mg DHA and EPA per 226 g serving, has a short-chain omega-3 to long-chain omega-3 ratio of about 0.3:1 by weight, and has an overall omega-6 to omega-3 ratio of about 1:4:1 by weight. Inositol is added to the Omega-6:3 PUFA Blend, or oils thereof, at a concentration of about 125 ppm, and vitamin E is added at a concentration of about 13 ppm.

The chicken nugget recipe may be completed by the addition of additional ingredients (new or previously included) in proportions necessary to maintain the omega-3 and omega-6 ratios and levels.

The chicken nugget food product may be completed by adding the Omega-6:3 PUFA Blend, or oils thereof, to a protein mix slurry comprised of ground chicken meats. The slurry is shaped into nuggets through an extruder. The chicken nugget pieces are battered and later breaded and fried through a continuous in-line system then packaged.

Turkey Breast Lunch Meat

Turkey breast lunch meats are readily known to one of ordinary skill in the art. The following list of ingredients is merely an illustrative example and is in no way meant to be limiting. An example turkey breast lunch meat product includes turkey breast halves, turkey breast tenderloins, desinewed turkey breast, turkey breast skin pieces, water, starch, salt, carrageenan gum, sodium lactate, salt, sugar, sodium tripolyphosphate, and sodium nitrate.

A turkey breast lunch meat food product with at least 1.6% by weight Omega-6:3 PUFA Blend, or oils thereof, delivers at least 101 mg DHA and EPA per 56 g serving, has a short-chain omega-3 to long-chain omega-3 ratio of about 1:61.3 by weight, and has an overall omega-6 to omega-3 ratio of about 0.001:119 by weight. Inositol is added to the Omega-6:3 PUFA Blend, or oils thereof, at a concentration of about 125 ppm, and vitamin E is added at a concentration of about 13 ppm.

The turkey breast lunch meat recipe may be completed by the addition of additional ingredients (new or previously included) in proportions necessary to maintain the omega-3 and omega-6 ratios and levels.

The turkey breast lunch meat food product may be completed by curing coarse ground turkey meat pieces in a pickling solution. Texture aid binding ingredients and Omega-6:3 PUFA Blend, or oils thereof, are added to the meat slurry in a mixer to create the desired texture. The meat slurry is molded into desired shapes then cooked, cooled, sliced and packaged.

Plain Yogurt

The composition of yogurt is readily known to one of ordinary skill in the art. The following list of ingredients is merely an illustrative example and is in no way meant to be limiting. An example yogurt product includes whey protein, and *Lactobacillus bulgaricus*.

A plain yogurt food product with at least 0.4% by weight Omega-6:3 PUFA Blend, or oils thereof, delivers about 109 mg DHA and EPA per 226 g serving, has a short-chain omega-3 to long-chain omega-3 ratio of about 1:1 by weight, and has an overall omega-6 to omega-3 ratio of about 0.7:1 by weight. Inositol is added to the Omega-6:3 PUFA Blend, or oils thereof, at a concentration of about 125 ppm, and vitamin E is added at a concentration of about 3 ppm.

The plain yogurt recipe may be completed by the addition of additional ingredients (new or previously included) in proportions necessary to maintain the omega-3 and omega-6 ratios and levels.

The plain yogurt food product may be completed by standardizing the milk and adding the Omega-6:3 PUFA Blend, or oils thereof. The enriched milk is pasteurized and homogenized before the cooling process. Culture is added to the milk in a fermentation tank set to about 110° F. Cups are filled, sealed, and moved to a fermentation room and held at about 105° F. for about 4 hours or until pH is below 4.6. The yogurt is placed in a cooler room for 24 hours.

Breakfast Items

Breakfast is typically the first meal taken after rising from a night's sleep, most often eaten in the early morning.

Liquid Egg Product

The composition of liquid eggs is readily known to one of ordinary skill in the art. The following list of ingredients is merely an illustrative example and is in no way meant to be limiting. An example of liquid egg product includes pasteurized whole eggs, water, pasteurized egg whites, salt, xanthan gum, sodium phosphate, butter flavoring, citric acid, and nisin.

A liquid egg food product with at least 1.4% by weight Omega-6:3 PUFA Blend, or oils thereof, delivers about 913 mg DHA and EPA per 70 g serving, has a short-chain omega-3 to long-chain omega-3 ratio of about 0.1:1 by weight, and has an overall omega-6 to omega-3 ratio of about 0.8:1 by weight. Inositol is added to the Omega-6:3 PUFA Blend, or oils thereof, at a concentration of about 125 ppm, and vitamin E is added at a concentration of about 114 ppm.

The liquid egg recipe may be completed by the addition of additional ingredients (new or previously included) in proportions necessary to maintain the omega-3 and omega-6 ratios and levels.

The liquid egg food product may be completed by breaking eggs and filtering at a cold temperature (about 4° C.). The Omega-6:3 PUFA Blend, or oils thereof, is added to liquid egg product by batch or inline addition with salt, sugar or other additives. The solid content is standardized and pasteurized at 74° C. to achieve treatment temperatures of 74° C. for a unique bacterial reduction (6 logs). The food product is homogenized and packed for storage at cooler temperatures or in freezers.

Liquid Egg White Product

The composition of liquid egg whites is readily known to one of ordinary skill in the art. The following list of ingredients is merely an illustrative example and is not way meant to be limiting. An example of liquid egg white product includes pasteurized egg whites, buttermilk, salt, xanthan gum, sodium phosphate, butter flavoring, citric acid, and raisin.

A liquid egg white food product with at least 4% by weight Omega-6:3 PUFA Blend, or oils thereof, delivers 110 mg DHA and EPA per 70 g serving, has a short-chain omega-3 to long-chain omega-3 ratio of about 0.02:1 by weight, and has an overall omega-6 to omega-3 ratio of about 0.1:1 by weight. Inositol is added to the Omega-6:3 PUFA Blend, or oils thereof, at a concentration of about 125 ppm, and vitamin E is added at a concentration of about 14 ppm.

The liquid egg white recipe may be completed by the addition of additional ingredients (new or previously included) in proportions necessary to maintain the omega-3 and omega-6 ratios and levels.

The liquid egg food product may be completed by breaking eggs, separating the yolk from the egg white, and filtering at a cold temperature (about 4° C.). The Omega-6:3 PUFA Blend, or oils thereof, is added to liquid egg product by batch or inline addition with salt, sugar or other additives. The solid content is standardized and pasteurized at 74° C. to achieve treatment temperatures of 74° C. for a unique bacterial reduction (6 logs). The food product is homogenized and packed for storage at cooler temperatures or in freezers.

Example Beverages

A beverage is defined as a drink that is prepared for human consumption.

Fruit Smoothie

The composition of fruit smoothies are readily known to one of ordinary skill in the art. The following list of ingredients is merely an illustrative example and is in no way meant to be limiting. As an example, a peach mango smoothie product includes water, sugar, citric acid, bipro isolated whey powder, fiber, glycerine, peach and mango flavoring, and oranges.

A fruit smoothie food product with at least 0.3% by weight Omega-6:3 PUFA Blend, or oils thereof, delivers about 110 mg DHA and EPA per 118 ml serving, has a short-chain omega-3 to long chain omega-3 ratio of about 1:11 by weight, and has an overall omega-6 to omega-3 ratio of about 0.5:1 by weight. Inositol is added to the Omega-6:3 PUFA Blend, or oils thereof, at a concentration of about 125 ppm, and vitamin E is added at a concentration of about 14 ppm.

The fruit smoothie recipe may be completed by the addition of additional ingredients (new or previously included) in proportions necessary to maintain the omega-3 and omega-6 ratios and levels.

The fruit smoothie food product may be completed by mixing water and the remaining water phase ingredients into a mixing kettle to make a homogenous water-based syrup. The water-based syrup is transferred to a mixing tank with the Omega-6:3 PUFA Blend, or oils thereof. The syrup is heated to a temperature of 190° F. and hot filled to appropriate bottles.

Flavored Beverages

The compositions of flavored beverages are readily known to one of ordinary skill in the art. The following list of ingredients is merely an illustrative example and is not way meant to be limiting. An example flavored beverage product includes pre-hydrated CMC 2500 powder TIC Gum, TIC ice, sucralose sweetener, and filtered drinking water.

A flavored beverage food product with at least 0.3% by weight Omega-6:3 PUFA Blend, or oils thereof, delivers about 110 mg DHA and EPA per 237 ml serving, has a short-chain omega-3 to long-chain omega-3 ratio of about 0.1:1 by weight, and has an overall omega-6 to omega-3 ratio of about 0.5:1 by weight. Inositol is added to the Omega-6:3 PUFA Blend, or oils thereof, at a concentration of about 125 ppm, and vitamin E is added at a concentration of about 14 ppm.

The flavored beverage recipe may be completed by the addition of additional ingredients (new or previously included) in proportions necessary to maintain the omega-3 and omega-6 ratios and levels.

The flavored beverage food product may be completed by mixing water and the remaining water phase ingredients into a mixing kettle to make a homogenous water-based syrup. The water-based syrup is transferred to a mixing tank with the Omega-6:3 PUFA Blend. The syrup is heated to a temperature of 190° F. and hot filled to appropriate bottles.

Orange Juice

The composition of orange juice is readily known to one of ordinary skill in the art. The following list of ingredients is merely an illustrative example and is not way meant to be limiting. An example orange juice product includes orange juice, pectin, and lecithin.

An orange juice food product with at least 0.3% by weight Omega-6:3 PUFA Blend, or oils thereof, delivers about 110 mg DHA and EPA per 8 oz, serving, has a short-chain omega-3 to long-chain omega-3 ratio of about 0.5:1 by weight, and has an overall omega-6 to omega-3 ratio of about 1.5:1 by weight. Inositol is added to the Omega-6:3 PUFA Blend, or oils thereof, at a concentration of about 125 ppm, and vitamin E is added at a concentration of about 14 ppm.

The orange recipe may be completed by the addition of additional ingredients (new or previously included) in proportions necessary to maintain the omega-3 and omega-6 ratios and levels.

The orange juice food product may be completed by cold pressing the oranges and filtering the extracted juice. After acidity and composition of the juice is adjusted, the Omega-6:3 PUFA Blend, or oils thereof, is added to the juice. The juice is packaged after low temperature pasteurization.

Italian Ice Beverage

The composition of Italian ice is readily known to one of ordinary skill in the art. The following list of ingredients is merely an illustrative example and is in no way meant to be limiting. An example Italian ice beverage product includes corn syrup, pre-hydrated CMC 2500 powder, TIC Ice, sugar, citric acid, coloring, and filtered drinking water.

An Italian ice beverage food product with at least 0.3% by weight Omega-6:3 PUFA Blend, or oils thereof, delivers about 110 mg DHA and EPA per 8 fluid oz. serving, has a short-chain omega-3 to long-chain omega-3 ratio of about 1:1 by weight, and has an overall omega-6 to omega-3 ratio of about 2:1 by weight. Inositol is added to the Omega-6:3

PUFA Blend, or oils thereof, at a concentration of about 125 ppm, and vitamin E is added at a concentration of about 14 ppm.

The Italian ice recipe may be completed by the addition of additional ingredients (new or previously included) in proportions necessary to maintain the omega-3 and omega-6 ratios and levels.

The Italian ice food product may be completed by mixing the Omega-6:3 PUFA Blend, or oils thereof, Italian ice mix, sugar and water in a high sheer blender to create a uniform mix. The slurry is then cooked to 190° F. The heat-processed mix is then put through a preliminary freezing process where the slurry temperature is decreased to 10° F. slushy/semi-solid form. This semi-solid product is packed into cups or turned into bars. The packed Italian ice goes through a second freezing or hard freezing process which is below −20° F.

Soy Milk

The composition of soy milk is readily known to one of ordinary skill in the art. The following list of ingredients is merely an illustrative example and is in no way meant to be limiting. An example soymilk product includes soy milk concentrate, water, sugar, carrageenan gum, salt, vanilla flavor, and calcium carbonate.

A soy milk food product with at least 4.4% by weight Omega-6:3 PUFA Blend, or oils thereof, delivers about 101 mg DHA and EPA per 8 fluid oz. serving, has a short-chain omega-3 to long-chain omega-3 ratio of about 1.6:1 by weight, and has an overall omega-6 to omega-3 ratio of about 5:1 by weight. Inositol is added to the Omega-6:3 PUFA Blend, or oils thereof, at a concentration of about 125 ppm, and vitamin E is added at a concentration of about 13 ppm.

The soy milk recipe may be completed by the addition of additional ingredients (new or previously included) in proportions necessary to maintain the omega-3 and omega-6 ratios and levels.

The soy milk food product may be completed by grinding soybeans soaked for 4-12 hours into a mash or pulp (Stone/manual grinding, electric blending etc.) with the addition of water. The resulting slurry is cooked in commercial steam injected vessels and separated from the remaining "Okara" fiber by filter press or centrifuge. The supernatant is pasteurized and the Omega-6:3 PUFA Blend, or oils thereof, is added to the water phase in a holding tank with a mixer. After homogenizing the mixture, filing, packaging and storage steps are performed.

Sports Drinks

The compositions of standard sport drinks are readily known to one of ordinary skill in the art. The following list of ingredients is merely an illustrative example and is in no way meant to be limiting. An example sports drink product includes fruit juice, salt, potassium chloride, lemon juice, and filtered drinking water.

A sports drink food product with at least 0.3% by weight Omega-6:3 PUFA Blend, or oils thereof, delivers about 101 mg DHA and EPA per 340 g serving, has a short chain omega-3 to long-chain omega-3 ratio of about 1:61 by weight, and has an overall omega-6 to omega-3 ratio of about 0.5:1 by weight. Inositol is added to the Omega-6:3 PUFA Blend, or oils thereof, at a concentration of about 125 ppm, and vitamin E is added at a concentration of about 13 ppm.

The sports drink recipe may be completed by the addition of additional ingredients (new or previously included) in proportions necessary to maintain the omega-3 and omega-6 ratios and levels.

The sports drink food product may be completed by mixing water and the remaining water phase ingredients into a mixing kettle to make a homogenous water-based syrup. The water-based syrup is transferred to a mixing tank with the Omega-6:3 PUFA Blend, or oils thereof. The syrup is heated to a temperature of 190° F. and hot filled to appropriate bottles.

Fully Described Embodiments

In one embodiment, the present invention relates to a food product comprising (a) omega-6 fatty acids, (b) omega-9 fatty acids, (c) omega-3 fatty acids that comprise a short-chain omega-3 polyunsaturated fatty acid ("PUFA") and a long-chain omega-3 PUFA, where the short-chain omega-3 PUFA has fewer than 20 carbon atoms in an aliphatic tail and the long-chain omega-3 PUFA has at least 20 carbons in an aliphatic tail; and an antioxidant; wherein the food product includes (i) between about 2 g and about 6 g of total fatty acids per 100 g of food product, (ii) between about 0.25 and about 1 g total omega-3 fatty acids per 100 g of food product, (iii) the ratio of omega-9 to omega-6 fatty acids, by weight, is from about 1:1 to about 4:1 and (iv) the ratio of omega-6 to omega-3 fatty acids, by weight, is from about 0.1:1 to about 2:1; and (v) the ratio of short-chain omega-3 PUFA to long-chain omega-3 PUFA, by weight, is from about 0.05:1 to about 2:1.

In a second embodiment, the present invention relates to a food product comprising (a) omega-6 fatty acids. (b) omega-9 fatty acids, (c) omega-3 fatty acids that comprise a short-chain omega-3 polyunsaturated fatty acid ("PUFA") and a long-chain omega-3 PUFA, where the short-chain omega-3 PUFA has fewer than 20 carbon atoms in an aliphatic tail and the long-chain omega-3 PUFA has at least 20 carbons in an aliphatic tail; and an antioxidant; wherein the food product includes (i) between about 2 g and about 6 g of total fatty acids per 100 g of food product, (ii) between about 0.25 and about 1 g total omega-3 fatty acids per 100 g of food product, (iii) the ratio of omega-9 to omega-6 fatty acids, by weight, is from about 0.1:1 to about 2:1 and (iv) the ratio of omega-6 to omega-3 fatty acids, by weight, is from about 0.5:1 to about 2:1; and (v) the ratio of short-chain omega-3 PUFA to long-chain omega-3 PUFA, by weight, is from about 0.01:1 to about 1:1.

In a third embodiment, the present invention relates to a food product comprising (a) omega-6 fatty acids, (b) omega-9 fatty acids, (c) omega-3 fatty acids that comprise a short-chain omega-3 polyunsaturated fatty acid ("PUFA") and a long-chain omega-3 PUFA, where the short-chain omega-3 PUFA has fewer than 20 carbon atoms in an aliphatic tail and the long-chain omega-3 PUFA has at least 20 carbons in an aliphatic tail; and an antioxidant; wherein the food product includes (i) between about 2 g and about 6 g of total fatty acids per 100 g of food product, (ii) between about 0.25 and about 1 g total omega-3 fatty acids per 100 g of food product, (iii) the ratio of omega-9 to omega-6 fatty acids, by weight, is from about 0.1:1 to about 2:1 and (iv) the ratio of omega-6 to omega-3 fatty acids, by weight, is from about 1:1 to about 2:1; and (v) the ratio of short-chain omega-3 PUFA to long-chain omega-3 PUFA, by weight, is from about 0.1:1 to about 1:1.

In a fourth embodiment, the present invention relates to a food product comprising (a) omega-6 fatty acids, (h) omega-9 fatty acids, (c) omega-3 fatty acids that comprise a short-chain omega-3 polyunsaturated fatty acid ("PUFA") and a long-chain omega-3 PUFA, where the short-chain omega-3 PUFA has fewer than 20 carbon atoms in an aliphatic tail and the long-chain omega-3 PUFA, has at least 20 carbons in an aliphatic tail; and an antioxidant; wherein the food product includes (i) between about 1 g and about 3 g of total fatty acids per 100 g of food product, (ii) between about 0.1 g and about 0.5 g total omega-3 fatty acids per 100 g of food product, (iii) the ratio of omega-9 to omega-6 fatty acids, by weight, is from about 1:1 to about 4:1 and (iv) the ratio of omega-6 to omega-3 fatty acids, by weight, is from about 0.1:1 to about 2:1; and (v) the ratio of short-chain omega-3 PUFA, to long-chain omega-3 PUFA, by weight, is from about 0.05:1 to about 2:1.

We claim:

1. A nutritional composition comprising a combination of fatty acids, the combination of fatty acids comprising:
   a. omega-3 fatty acids comprising
      i. alpha-linolenic acid (ALA) and
      ii. eicosapentaenoic acid (EPA), docosahexaenoic acid (DHA), or a combination of EPA and DHA;
   b. omega-6 fatty acids comprising linoleic acid; and
   c. omega-9 fatty acids comprising oleic acid;
wherein the composition comprises weight ratios of:
   d. omega-6 fatty acids to omega-3 fatty acids ranging from about 0.01:1 to about 4:1, respectively;
   e. omega-9 fatty acids to omega-3 fatty acids ranging from about 1:1 to about 4:1, respectively; and
   f. ALA to EPA, DHA, or the combination of EPA and DHA ranging from about 0.01:1 to about 5:1, respectively.

2. The nutritional composition of claim 1, wherein the weight ratios of omega-6 fatty acids to omega-3 fatty acids range from about 0.01:1 to about 1:1, respectively.

3. The nutritional composition of claim 2, wherein the weight ratios of omega-6 fatty acids to omega-3 fatty acids range from about 0.01:1 to about 0.5:1, respectively.

4. The nutritional composition of claim 3, wherein the composition comprises at least 50 mg of EPA per standard serving, or 50 mg of DHA per standard serving, or 50 mg of the combination of EPA and DHA per standard serving.

5. The nutritional composition of claim 4, wherein the composition comprises at least about 130 mg of EPA or DHA or a combination of EPA and DHA per standard serving.

6. The nutritional composition of claim 1, wherein the composition is in a functional food, a beverage, a nutritional supplement, or a pharmaceutical.

7. The nutritional composition of claim 1, wherein arachidonic acid is present in no more than about 5% by weight of the omega-6 fatty acid present in the composition.

8. The nutritional composition of claim 1, further comprising medium chain triglycerides at a weight ratio to EPA, DHA, or a combination of EPA and DHA of about 0.01:1 to about 4:1, respectively.

9. The nutritional composition of claim 1, further comprising an antioxidant.

10. The nutritional composition of claim 9, wherein the antioxidant is selected from the group consisting of (a) inositol, (b) one or more tocopherals, (c) a curcumin C3 complex, (d) manganese oxide, (e) rosemary, (f) butylated hydroxyanisole (BHA), (g) butylated hydroxytoluene (BHT), (h) tert-butylhydroquinone (TBHQ), (i) a polyphenol, such as, e.g., curcumin, (j) propyl gallate, (k) ethoxyquin, (l) ascorbic acid, (m) a sinapyl compound, (n) ferulic acid, (o) sulforaphane, and (p) one or more glucosinates.

11. The nutritional composition of claim 1, wherein the weight ratio of omega-6 fatty acids to ALA is less than about 3:1.

12. A nutritional composition comprising:
   a. Water
   b. Protein
   c. A combination of fatty acids comprising
      1. omega-3 fatty acids comprising
         (i) alpha-linolenic acid (ALA) and
         (ii) eicosapentaenoic acid (EPA), docosahexaenoic acid (DHA), or a combination of EPA and DHA;
      2. omega-6 fatty acids comprising linoleic acid; and
      3. omega-9 fatty acids comprising oleic acid;
wherein the combination of fatty acids comprises weight ratios of:
   d. omega-6 fatty acids to omega-3 fatty acids of from about 1:1 to about 3:1; and
   e. ALA to EPA, DHA, or the combination of EPA and DHA of from about 0.01:1 to about 5:1.

13. The nutritional composition of claim 12, wherein the composition comprises a weight ratio of omega-9 fatty acids to omega-3 fatty acids of from about 1:1 to about 4:1, respectively.

14. The nutritional composition of claim 12, wherein the protein is whey protein.

15. The nutritional composition of claim 12, further comprising medium chain triglycerides (MCT).

16. The nutritional composition of claim 15, wherein the combination of fatty acids comprises a weight ratio of MCT to eicosapentaenoic acid (EPA), docosahexaenoic acid (DHA), or a combination of EPA and DHA of about 0.01:1 to about 4:1, respectively.

17. The nutritional composition of claim 12, further comprising an antioxidant.

18. The nutritional composition of claim 17, wherein the antioxidant is selected from the group consisting of (a) inositol, (b) one or more tocopherals, (c) a curcumin C3 complex, (d) manganese oxide, (e) rosemary, (f) butylated hydroxyanisole (BHA), (g) butylated hydroxytoluene (BHT), (h) tert-butylhydroquinone (TBHQ), (i) a polyphenol, such as, e.g., curcumin, (j) propyl gallate, (k) ethoxyquin, (l) ascorbic acid, (m) a sinapyl compound, (n) ferulic acid, (o) sulforaphane, and (p) one or more glucosinates.

19. The nutritional composition of claim 12, wherein the composition comprises at least about 50 mg of EPA or DHA or a combination of EPA and DHA per standard serving.

20. The nutritional composition of claim 12, wherein the composition comprises at least about 130 mg of EPA or DHA or a combination of EPA and DHA per standard serving.

21. The nutritional composition of claim 12, further comprising a vitamin.

22. A nutritional composition comprising:
   a. Water
   b. Protein
   c. A combination of fatty acids comprising:
      1. omega-3 fatty acids comprising
         (i) alpha-linolenic acid (ALA) and
         (ii) eicosapentaenoic acid (EPA), docosahexaenoic acid (DHA), or a combination of EPA and DHA;
      2. omega-6 fatty acids comprising linoleic acid; and
      3. omega-9 fatty acids comprising oleic acid;
wherein the combination of fatty acids comprises weight ratios of:
   d. omega-6 fatty acids to omega-3 fatty acids of from about 0.01:1 to about 4:1, respectively;
   e. omega-9 fatty acids to omega-3 fatty acids ranging from about 1:1 to about 4:1, respectively; and
   f. ALA to EPA, DHA, or the combination of EPA and DHA ranging from about 0.01:1 to about 5:1, respectively.

23. The nutritional composition of claim 22, wherein the protein is whey protein.

24. The nutritional composition of claim 22, further comprising medium chain triglycerides (MCT).

25. The nutritional composition of claim 24, wherein the combination of fatty acids comprises a weight ratio of MCT to eicosapentaenoic acid (EPA), docosahexaenoic acid (DHA), or a combination of EPA and DHA of about 0.01:1 to about 4:1.

26. The nutritional composition of claim 22, further comprising an antioxidant.

27. The nutritional composition of claim 26, wherein the antioxidant is selected from the group consisting of (a) inositol, (b) one or more tocopherols, (c) a curcumin C3 complex, (d) manganese oxide, (e) rosemary, (f) butylated hydroxyanisole (BHA), (g) butylated hydroxytoluene (BHT), (h) tert-butylhydroquinone (TBHQ), (i) a polyphenol, such as, e.g., curcumin, (j) propyl gallate, (k) ethoxyquin, (l) ascorbic acid, (m) a sinapyl compound, (n) ferulic acid, (o) sulforaphane, and (p) one or more glucosinates.

28. The nutritional composition of claim 22, wherein the composition comprises at least about 50 mg of EPA or DHA or a combination of EPA and DHA per standard serving.

29. The nutritional composition of claim 22, wherein the composition comprises at least about 130 mg of EPA or DHA or a combination of EPA and DHA per standard serving.

30. The nutritional composition of claim 22, further comprising a vitamin.

\* \* \* \* \*